US010405751B2

United States Patent
Hanlon et al.

(10) Patent No.: US 10,405,751 B2
(45) Date of Patent: *Sep. 10, 2019

(54) SPECTROSCOPIC DETECTION OF BRAIN DAMAGE

(71) Applicant: THE UNITED STATES OF AMERICA AS REPRESENTED BY THE DEPARTMENT OF VETERANS AFFAIRS, Washington, DC (US)

(72) Inventors: Eugene B. Hanlon, Bedford, MA (US); Frank A. Greco, Bedford, MA (US)

(73) Assignee: The United States of America As Represented By The Department Of Vetern Affairs, Washington, DC (US)

(*) Notice: Subject to any disclaimer, the term of this patent is extended or adjusted under 35 U.S.C. 154(b) by 1092 days.

This patent is subject to a terminal disclaimer.

(21) Appl. No.: 14/539,950

(22) Filed: Nov. 12, 2014

(65) Prior Publication Data

US 2015/0073282 A1    Mar. 12, 2015

Related U.S. Application Data

(63) Continuation of application No. 12/462,886, filed on Aug. 10, 2009, now Pat. No. 8,954,133.

(60) Provisional application No. 61/087,470, filed on Aug. 8, 2008.

(51) Int. Cl.
A61B 6/00       (2006.01)
A61B 5/00       (2006.01)

(52) U.S. Cl.
CPC .......... *A61B 5/0075* (2013.01); *A61B 5/4064* (2013.01); *A61B 5/4088* (2013.01); *A61B 5/7264* (2013.01); *A61B 5/0037* (2013.01)

(58) Field of Classification Search
CPC ... A61B 5/0037; A61B 5/0075; A61B 5/4064; A61B 5/4088; A61B 5/7264
See application file for complete search history.

(56) References Cited

U.S. PATENT DOCUMENTS

| | | |
|---|---|---|
| 6,421,553 B1 | 7/2002 | Costa et al. |
| 7,192,783 B2 | 3/2007 | Alfano et al. |
| 2003/0009104 A1 | 1/2003 | Hyman et al. |
| 2003/0195431 A1 | 10/2003 | Sukhatme |
| 2004/0073119 A1 | 4/2004 | Mycek et al. |
| 2009/0221919 A1 | 9/2009 | Ben Dor et al. |

FOREIGN PATENT DOCUMENTS

WO    WO 2006/047477    5/2006

OTHER PUBLICATIONS

Farrell, Thomas J. and Michael S. Patterson, "A diffusion theory model of spatially resolved, steady-state diffuse reflectance for the noninvasive determination of tissue optical properties in vivo," *Medical Physics*, 1992, 19:879-88.

Fischer, P. et al., "Conversion from subtypes of mild cognitive impairment to Alzheimer dementia," *Neurology*, 2007, 68:288-91.

(Continued)

*Primary Examiner* — Christopher L Cook
(74) *Attorney, Agent, or Firm* — Ballard Spahr LLP

(57) ABSTRACT

The present invention provides a non-invasive device and method of detecting or evaluating brain damage in a living subject.

19 Claims, 12 Drawing Sheets
(10 of 12 Drawing Sheet(s) Filed in Color)

(56) References Cited

OTHER PUBLICATIONS

Hanlon, Eugene B. et al., "Near-Infrared Fluorescence Spectroscopy Detects Alzheimer's Disease In Vitro," *Photochemistry and Photobiology*, 1999, 70:236-42.

Hintersteiner, Martin et al., "In vivo detection of amyloid-b deposits by near-infrared imaging using an oxazine-derivative probe," *Nature Biotechnology*, 2005, 23:577-83.

Hock, Christoph et al., "Decrease in parietal cerebral hemoglobin oxygenation during performance of a verbal fluency task in patients with Alzheimer's disease monitored by means of near-infrared spectroscopy (NIRS)—correlation with simultaneous rCBF-PET measurements," *Brain Research*, 1997, 755:293-303.

Hyman, B. T. et al., "Quantitative analysis of senile plaques in Alzheimer disease: Observation of log-normal size distribution and molecular epidemiology of differences associated with apolipoprotein E genotype and trisomy 21 (Down syndrome)," *Proc. Natl. Acad. Sci. USA*, 1995, 92:3586-90.

Irizarry, Michael C. and Bradley T. Hyman, "Alzheimer Disease Therapeutics," *Journal of Neuropathology and Experimental Neurology*, 2001, 60:923-8.

Jack, C. R., Jr., et al., "Brain atrophy rates predict subsequent clinical conversion in normal elderly and amnestic MCI," *Neurology*, 2005, 65:1227-31.

Jöbsis, Frans F., "Noninvasive, Infrared Monitoring of Cerebral and Myocardial Oxygen Sufficiency and Circulatory Parameters," *Science*, 1977, 198:1264-7.

Love, S., "Neuropathological Investigation of Dementia: A Guide for Neurologists," *J Neural Neurosurg Psychiatry*, 2005, 76:v8-14.

Machulda, M. M. et al., "Comparison of memory fMRI response among normal, MCI, and Alzheimer's patients," *Neurology*, 2003, 61:500-6.

Morris, John C. and Joseph L. Price, "Pathologic Correlates of Nondemented Aging, Mild Cognitive Impairment, and Early-Stage Alzheimer's Disease," *Journal of Molecular Neuroscience*, 2001, 17:101-118.

Skoch, Jesse et al., "Development of an optical approach for noninvasive imaging of Alzheimer's disease pathology," *Journal of Biomedical Optics*, 2005, 10:011007-1-7.

Strangman, Gary et al., "A Quantitative Comparison of Simultaneous BOLD fMRI and NIRS Recordings during Functional Brain Activation," *NeuroImage*, 2002, 17:719-31.

Hanlon, Eugene B. et al., "Scattering differentiates Alzheimer disease in vitro," *Optics Letters*, 2008, 33:624-6.

Hanlon, Eugene B. et al., "Optical spectroscopy to diagnose Alzheimer's disease in vivo," *Optical Society of America*, 2003, pp. 1-3.

Hanlon, Eugene B. et al., "Light Scattering Spectroscopy Detects Changes in Alzheimer's Brain," *Optical Society of America*, 2000, pp. 1-3.

Hanlon, Gene and G. R. Harrision, "Optical Spectroscopy to Diagnose Alzheimer's Disease," 1999, pp. 1, 5 and 8-9.

Johns, Maureen et al., "Computational and In Vivo Investigation of Optical Reflectance from Human Brain to Assist Neurosurgery," *Journal of Biomedical Optics*, 1998, 3:437-45.

McIntosh, Laura M. et al., "Towards Non-Invasive Screening of Skin Lesions by Near-Infrared Spectroscopy," *J Invest Dermatol*, 2001, 116:175-81.

Mean spectra and standard error for AD (top), MCI (middle) and Control (bottom).

Relative intensity of AD spectra vs. Control spectra as a function of s-d.

Relative intensity of MCI spectra vs. Control spectra as a function of s-d.

US 10,405,751 B2

SPECTROSCOPIC DETECTION OF BRAIN DAMAGE

This patent application is a continuation application of U.S. Ser. No. 12/462,886, filed Aug. 10, 2009, which claims the priority of provisional application U.S. Ser. No. 61/087,470, filed Aug. 8, 2008, the contents of which are incorporated by reference into the present application.

The invention disclosed herein was made with government support under Merit Review Grant Nos. TAB1/HANLON/NEUD/F07, TAB4/HANLON/NEUD/S04 and TAB5/HANLON/NEUD/F99 awarded by the Department of Veterans Affairs. The government has certain rights in this invention.

Throughout this application various publications are referenced. The disclosures of these publications in their entireties are hereby incorporated by reference into this application in order to more fully describe the state of the art to which this invention pertains.

FIELD OF THE INVENTION

The field of the present invention relates to spectroscopic devices and methods of detecting brain damage from disease, such as Alzheimer's disease, or brain injury, such as traumatic brain injury.

BACKGROUND OF THE INVENTION

Alzheimer's disease (AD), the most common form of dementia seen in clinical practice, is a progressive, terminal, neurodegenerative disorder. The largest risk factor for Alzheimer disease (AD) is advanced age, and the public health impact of AD and related disorders is increasing in proportion to the increasing numbers of elderly. Alzheimer disease presents clinically as progressive memory loss but the only definitive diagnostic tests that now exist require neuropathologic examination of brain tissue, conducted almost exclusively postmortem.

As knowledge of the molecular features of AD and related neurodegenerative disorders advances, strategies for pharmaceutical interventions that implement this knowledge are being vigorously pursued [Irizarry et al., 2001]. However, there is currently no method for monitoring pathogenic response to such interventions in human clinical trials or for definitively diagnosing these disorders at an early stage, when intervention could be most beneficial.

There are now numerous articles documenting efforts to apply conventional medical imaging techniques to the diagnosis and monitoring of AD [Coimbra et al., 2006]. Magnetic resonance imaging (MRI) has provided a wealth of functional [Malchulda et al., 2003] and anatomic [Jack et al., 2005] information. The development of radionuclide markers targeting parenchymal amyloid deposits is a breakthrough in the application of positron emission tomography (PET) [Mathis et al., 2004]. And optical techniques, while not yet as widely applied in clinical practice as MRI or PET, have made parallel contributions to these efforts, utilizing functional information [Hock et al., 1997; Strangman et al., 2002] or exogenous markers in mice [Hintersteiner et al., 2005; Skoch et al.].

The expression "near-infrared window" describes the biomedically useful property of near-infrared light [Jobsis-vander Vliet, 1999] that it can propagate harmlessly several centimeters through living tissue and provide diagnostically valuable physical and chemical information by means of spectroscopic analysis [Jobsis, 1977].

The definitive neuropathologic features that distinguish a brain damaged from Alzheimer's Disease (AD) from normal brain (non-AD), are neuritic plaques (NP) and neurofibrillary tangles (NFT). Neuritic plaques are predominantly extra-cellular deposits of β-amyloid peptide fibrils and NFT are intra-neuronal accumulations of abnormally phosphorylated and oxidized tau protein. Currently, definitive diagnosis of Alzheimer disease relies upon postmortem detection of cortical neuritic plaques and neurofibrillary tangles [Love, 2005]. Routinely, histological sectioning and staining are required to detect these structures against the neuropil background.

Perelman (1998) described a non-invasive optical spectroscopy technique to detect dysplasia in Barrett's esophagus based on light scattering by epithelial cell nuclei.

There remains a need for non-invasively detecting brain disease or injury (including Alzheimer disease) in vivo.

SUMMARY OF THE INVENTION

The present invention provides non-invasive devices and methods for detecting, e.g., cortical neuritic plaques (NP), Lewy bodies, and/or neurofibrillary tangles (NFT) associated with brain damage (e.g., brain disease or injury), in a subject in vivo.

The present invention provides non invasive devices and methods of detecting or evaluating brain damage such as disease or brain injury, in a subject, using optical spectroscopy. In a method of the invention, the subject's head is exposed to a source of near-infrared light, (for example, in the range of wavelengths of 610-1030 nm) and the absorbance, transmission and/or reflectance of this light is measured after it propagates through the subject's head at various distances from the light source, constituting various spectra. These spectra are characterized by calculating the intensity and spectroscopic lineshape (the wavelength dependent distribution of intensity within each spectrum). The characteristic information for the subject, derived from the spectra, is represented as a numerical value or spatial coordinate value. The representations so derived from the spectra in the method of the invention correlate with characteristic information from normal subjects and to characteristic information known to be correlated with specific brain damage. Finally, the brain disease or injury is detected or evaluated by applying an algorithm as shown for example in Examples 2-7.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Definitions

Figure 1:
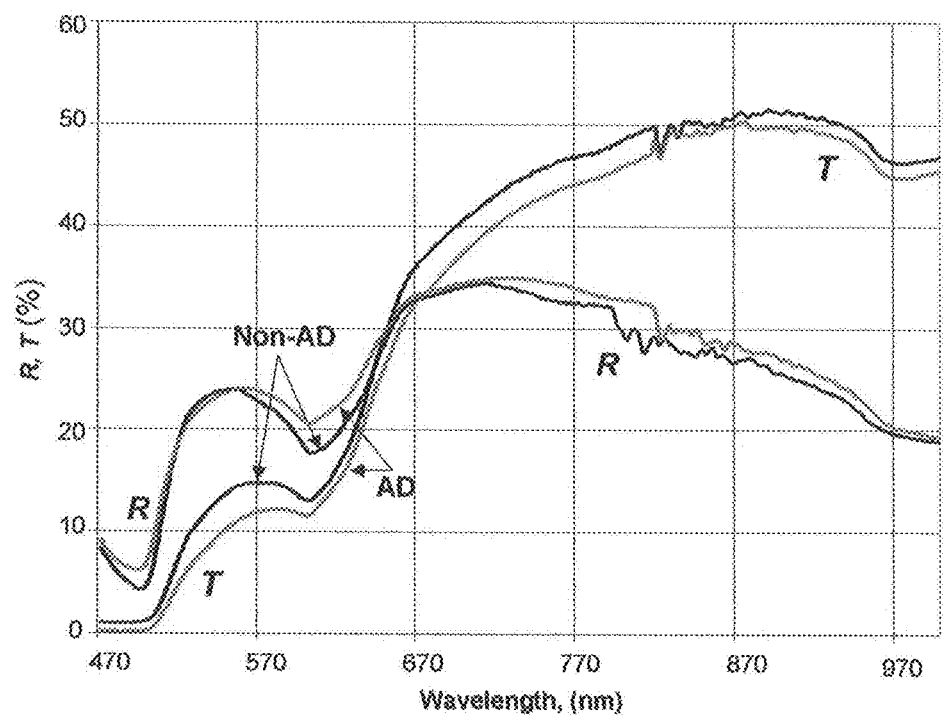
FIG. 1. Total reflectance (R) and transmission (T) spectra, acquired with an integrating sphere, of 1 mm thick brain tissue slabs from neuropathologically confirmed AD and non-AD cases, as described in Example 1, infra.

The term "NINCDS-ADRDA" refers to a set of neuropsychological criteria for the clinical assessment or diagnosis of probable AD (definitive diagnosis of AD requires histopathologic confirmation). The criteria require that the presence of cognitive impairment and a suspected dementia syndrome be confirmed by neuropsychological testing. Eight cognitive domains are assessed that may be impaired in AD: memory, language, perceptual skills, attention, constructive abilities, orientation, problem solving and functional abilities.

The term "brain damage" refers to conditions affecting a subject's brain where the brain structure is altered such that light spectra through the brain are also altered. Brain damage includes "brain disease" or "brain dysfunction" which refers to conditions affecting a subject's brain where the brain structure and/or biochemical composition is altered, for example by abnormal accumulation or deposits of proteins or other molecules. Brain diseases include, but are not limited to: tumors (e.g., gliomas, metastatic tumors, etc.); Pick's Disease; dementia related to alcoholism or exposure to heavy metals (e.g., arsenic, antimony, bismuth); dementia related to infectious diseases (e.g., by viruses (HIV, viral encephalitis), spirochetes (Lyme disease, syphilis) or prions (CJD)); AD, mild cognitive impairment (MCI), dementia with Lewy bodies (DLB), and Parkinson disease (PD). Brain damage also includes "brain injury" which refers to physical injuries to a subject's brain where the brain structure is altered, for example by: disruption of neuronal cell bodies; hemorrhage; diffuse axonal injuries accompanied by increased beta-amyloid and plaques and re-arrangement of axonal structure within the brain tissue; and hydrocephalus. Examples of brain injury include, but are not limited to, diffuse or mild traumatic brain injury (TBI), Multi-infarct dementia (MID) (also known as vascular dementia) and subdural hematoma.

For example, in the brain of a subject suffering AD, the brain may contain extracellular deposits of β-amyloid peptide fibrils which form neuritic plaques, and neurofibrillary tangles are formed from intra-neuronal accumulations of abnormally phosphorylated and oxidized tau protein. In the brain of a subject with Lewy Bodies (e.g., subjects suffering Parkinson disease, Lewy Body Dementia, Fronto-temporal Dementia with Lewy Bodies, etc.) aggregates of abnormal protein form proteinaceous cytoplasmic inclusions called Lewy Bodies may be found. In the brain of a subject suffering Creutzfeldt-Jakob disease (CJD), proteins form amyloid folds in which the proteins polymerise into aggregates consisting of tightly packed beta sheets may be found. Other alterations or deposits in the brain include, but are not limited to, lipofuscin granules, amyloid derived diffusible ligands (ADDLs) and neuropil threads.

Whether a difference between data is "statistically significant" or not, can be indicated by a p-value. A p-value of less than 0.05 is deemed statistically significant.

The term "scd" refers to the source-collection distance between the point or region at which the source light is incident upon the subject and the point or region at which the reflected, transmitted and/or emitted light is collected for analysis.

The term "spectrum" refers to a light spectrum measuring the absorbance, transmission, emission, scattering and/or reflectance of a light after it propagates through a subject. "Spectra," the plural of spectrum, may be characterized by calculating intensity, spectroscopic lineshape (e.g. in one embodiment the wavelength dependent distribution of intensity within each spectrum, i.e. the intraspectrum wavelength dependent relative intensity), and/or mathematical modeling using measurement variables such as the optical properties of the tissue, the scd, etc. and theories of light propagation and absorbance, transmission, emission, scattering and/or reflectance of a light after it propagates through a human tissue structure. Raman spectra are (generally molecular) vibrational spectra (similar to near-infrared absorption spectra) derived from measurements of the wavelength difference between the incident light (i.e., source light, usually laser light) and inelastically scattered light (i.e., detected light that has exchanged energy with matter (i.e., the object of analysis). Generally, the Raman spectrum of a pure compound is unique to the molecular structure of the compound; the Raman spectrum of a complex material, such as biological tissue, is a linear or non-linear combination of the spectra of the individual molecular constituents of the material.

Methods of the Invention

The present invention relates to a method of detecting or evaluating brain damage, such as a brain disease, or a brain injury, in a subject.

Figure 11:
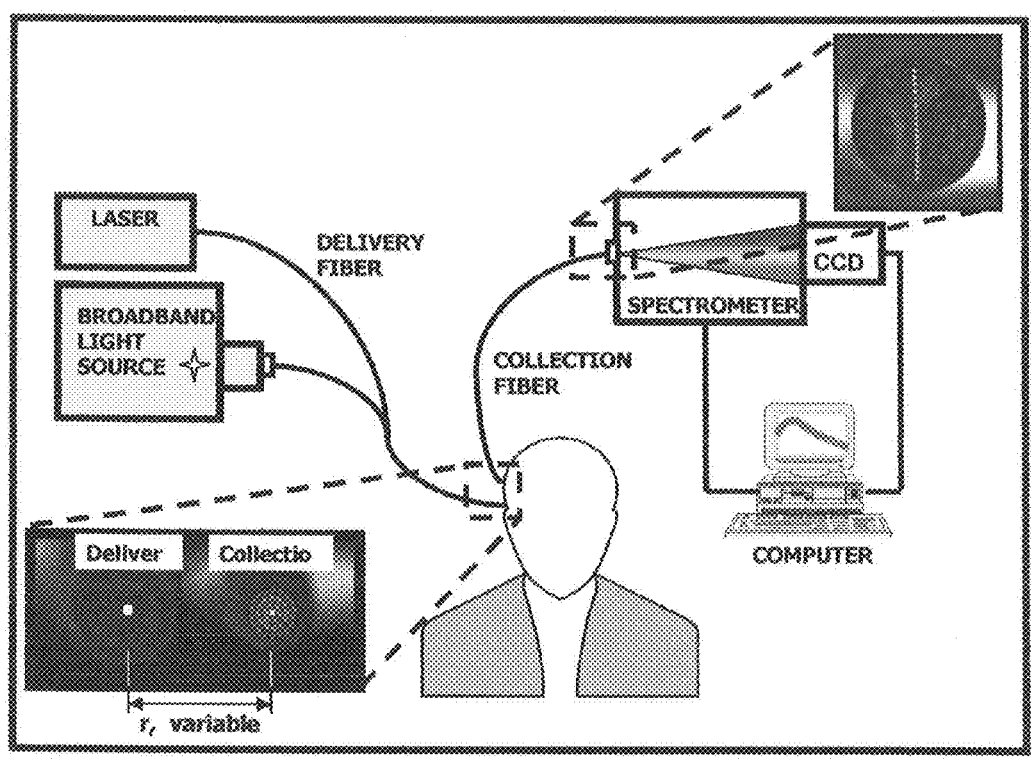
FIG. 11 shows a visual depiction of how a device is attached to a subject to effect an embodiment of the invention.

In one embodiment of this method, a part of the subject's head, for example, the subject's temple, is selected and is exposed to a light source emitting light in the visible through near-infrared wavelength range (e.g., from about 400 to 2200 nm), in a range of e.g., about one millisecond to 10 seconds so as to produce spectra. The temple may be selected because of early involvement of the temporal cortex in AD or Parkinson disease; the subject's fronto-temporal region may be selected in subjects suffering from fronto-temporal dementias. In subjects with traumatic brain injury, multiple sites over the entire head may be examined. FIG. 11 shows a visual depiction of how a device may be attached to a subject to carry out an embodiment of the invention.

As those skilled in the art will appreciate, the exposure time to the light source is designed to maximize the signal-to-noise ratio of the spectrum being recorded, while remaining in the linear dynamic range of the detector, as described in Example 2, below. More specifically, the subject may be exposed to light emitted in the visible through near-infrared wavelength range in the range of about 400 to 2250, 400-2200, 435-2250 nm, 350-750 nm, 350-950 nm, about 450-850 nm, about 486-1037 nm, about 550-950 nm, about 550-1150 nm, about 610-1030 nm, about 644-1053 nm, about 650-1050 nm, about 650-1250 nm, about 750-1150 nm, about 750-1350 nm, about 850-1250 nm, about 850-1450 nm, about 950-1350 nm, about 950-1550 nm, about 1050-1450 nm, about 1050-1650 nm, about 1150-1550 nm, about 1150-1750 nm, about 1250-1650 nm, about 1250-1850 nm, about 1350-1750 nm, about 1350-1950 nm, about 1450-1850 nm, about 1450-2050 nm, about 1550-1950 nm, about 1550-2150 nm, about 1650-2050 nm, about 1650-2250 nm, about 1750-2150 nm and/or about 1850-2250 nm.

After exposure of the subject's head to a specified range of light, the light is transmitted, absorbed and/or reflected from the subject. The transmission, absorbance and/or reflectance of this light, recorded at a resolution, e.g., of about every 0.1 nm to 4 nm in the desired range, is detected and measured as or after it propagates through the subject's head. Detection and measurement of the light can be performed at various distances from the subject as or after the light propagates through the subject's head. The light detected and measured may be composed of various spectra. In one embodiment, the spectra can be fluorescence spectra or Raman spectra.

The spectra measured in this method may be characterized by calculating the intensity and spectroscopic lineshape (the wavelength dependent distribution of intensity within each spectrum) as described in the formulae in Examples 1-7, or by alternative methods such as Principal Component Analysis, Logistic Regression [Brown 1995; Kleinbaum et al., 1988], Linear Discriminant Analysis [Fisher, 1936] or mathematical modeling as described in Examples 5, 6, 7, infra.

A numerical value may be assigned to the data so characterized. This may be done by: i) correlating the newly obtained data from the subject to corresponding light transmission, absorbance or reflectance data obtained from control subjects (known not to have the disease or injury in question) and/or ii) fitting a theoretical model of the spectra expected when the disease or injury in question is present or absent to the data obtained from the subject, as described in Examples 5, 6, 7, infra.

For example, FIG. 11 shows a visual depiction of how a device may be attached to a subject to effect an embodiment of the invention. The step described above may be combined with other known methods of detecting or evaluating a brain disease or a brain injury in a living subject, such as the assessment of cognitive deficits in the subject to augment a diagnosis of a disease or injury using the methods of the invention. For example, in addition to a neuropsychological assessment of cognitive deficits in a subject, the present invention can help in the diagnosis of AD as the methods of the invention can non-invasively determine structural differences between a brain with plaques and tangles and a brain without plaques and tangles. Currently, only a biopsy or post mortem histopathological analysis of the brain can determine the presence of plaques and tangles needed for a definitive diagnosis of AD, an assessment of cognitive deficits in a subject can only predict the probability of AD.

In another embodiment of the invention, the non-invasive method of detecting or evaluating brain damage in a living subject comprises the steps of (a) exposing a part of the subject's head to a light source emitting light in the visible through near-infrared wavelength range so as to produce spectra; (b) characterizing the spectra by calculating the intensity and the spectroscopic lineshape from the data produced in step (a); (c) calculating a reduced scattering coefficient from the data in step (b); (d) assigning a numerical value to the reduced scattering coefficient calculated in step c) such that when compared to numerical values obtained from control subjects known not to have brain damage in question and to brain damaged subjects, a significant difference (e.g., a statistically significant difference) in the numerical values for brain damaged subjects and control subjects being indicative of brain damage so as to thereby detect or evaluate the brain damage in the living subject.

In a further embodiment of the invention, the method comprises: (a) exposing a part of the subject's head to a light source emitting light in the visible through near-infrared wavelength range so as to produce spectra; (b) characterizing the spectra by calculating the intensity and the spectroscopic lineshape from the data produced in step a); (c) calculating a scattering coefficient from the data in step (b); (d) calculating the size, shape, number density and relative refractive index of scattering particles from data in steps (b) and (c); (e) assigning numerical values to size(s), shape(s), number density(ies) and relative refractive index(ices) of scattering particles calculated from d) such that when compared to numerical values obtained from control subjects known not to have brain damage in question and to brain damaged subjects, a significant difference (e.g., a statistically significant difference) in the numerical values for brain damaged subject(s) and control subject(s) is indicative of brain damage.

In yet a further embodiment, the method comprises: (a) exposing a part of the subject's head to a light source emitting light in the visible through near-infrared wavelength range so as to produce spectra; (b) characterizing the spectra by calculating the intensity and the spectroscopic lineshape from the data produced in step a); (c) calculating a scattering coefficient from the data in step (b); (d) calculating the size, shape, and number density of scattering particles from data in steps (b) and (c); (e) assigning numerical values to size(s), shape(s), and number density(ies) of scattering particles calculated from d) such that when compared to numerical values obtained from control subject(s) known not to have brain damage in question and to brain damaged subjects, a significant difference (e.g., a statistically significant difference) in the numerical values for brain damaged subject(s) and control subject(s) being indicative of brain damage.

There are many formulae for calculating the intensity and spectroscopic lineshape (the wavelength dependent distribution of intensity within each spectrum) (e.g., see Examples 1-2 and 4-6). For example, the "shutter closed" data ($S_A$) may be subtracted from the corresponding "shutter opened" data ($S_L$) for each acquisition of each type of data (reference and patient), $$S_A = A(\lambda) r(\lambda) D(\lambda) t$$

$$S_L = [I_0(\lambda) + A(\lambda)] r(\lambda) D(\lambda) t,$$

where $I_0(\lambda)$ is the source light intensity incident on the target, $A(\lambda)$ is the ambient light intensity incident on the target, $r(\lambda)$ is the reflectance of the target, $D(\lambda)$ is the detector response function and t is the total exposure time, producing a background corrected (c) reference (R) spectrum for each source (s)

$$_s^c S_R(\lambda) = {}^s I_0(\lambda) r_R(\lambda) D(\lambda) t_R,$$

and a background corrected patient spectrum for each source, at each scd (i), on each temple (l, d) of each patient (P).

$$_s^{l,d,c} S_P^i(\lambda) = {}^s I_0(\lambda)^{l,d} r_P^i(\lambda) D(\lambda)_s^{l,d} t_P^i.$$

In one example, the reference spectra for each source were normalized to unit integrated intensity, yielding the normalized reference spectra, ${}^N S_R(\lambda)$ $$^N S_R(\lambda) = {}^c S_R(\lambda)/t_R \int {}^c S_R(\lambda) d\lambda = \frac{I_0(\lambda) \, r_R(\lambda) \, D(\lambda) \, t_R}{\int {}^c S_R(\lambda) d\lambda \cdot t_R},$$

where the indices l, d, s and i have been dropped to simplify notation. The intensities of the background corrected patient spectra were rectified for exposure time, $$_s^{l,d,t} S_P^i = {}_s^{l,d,c} S_P^i / {}_s^{l,d} t_P^i.$$

The diagnostic patient spectrum, $S_P$, is $$S_P = {}^t S_P / {}^N S_R$$

$$= I_0(\lambda) \, r_P(\lambda) \, D(\lambda) \left[ \frac{I_0(\lambda) \, r_R(\lambda) \, D(\lambda)}{\int {}^c S_R(\lambda) d\lambda} \right]^{-1}$$

$$= r_P(\lambda) \cdot \int {}^c S_R(\lambda) d\lambda,$$

where again, the indices l, d, s and i have been dropped to simplify notation.

Additionally, in accordance with the practice of the invention, the invention includes assigning a numerical value to the data. For example, the coordinates ($I_{\lambda(max)}$, $I_{\lambda(max)}/I_{\lambda(min)}$) may be calculated from $S_P$, $$I_{\lambda(max)} = \langle [I_{\lambda(799.35)}, I_{\lambda(800.99)}] \rangle \text{ and } I_{\lambda(min)} = \langle [I_{\lambda(970.12)}, I_{\lambda(974.88)}] \rangle,$$

where $\langle \rangle$ indicates the average value over the interval.

The numerical measures were determined from the intensity at the wavelength of maximum intensity ($I_{\lambda(max)}$) and the ratio of the intensities ($I_{\lambda(max)}/I_{\lambda(min)}$) at the wavelength of maximum intensity and the long wavelength minimum, for each $S_p$ of each patient at each scd as follows.

A scatter plot of the coordinates ($I_{\lambda(max)}$, $I_{\lambda(max)}/I_{\lambda(min)}$) differentiates $S_P$ of patients with different diagnoses. If the equation of the cut-off line is in the form, y=mx+b, then for each point in the scatter plot the perpendicular distance, r, from the point (x, y) to the cut-off line is given by the expression $$r = x(m/\sqrt{m^2+1}) + y(1/\sqrt{m^2+1}) - b/\sqrt{m^2+1}$$

Figure 6:
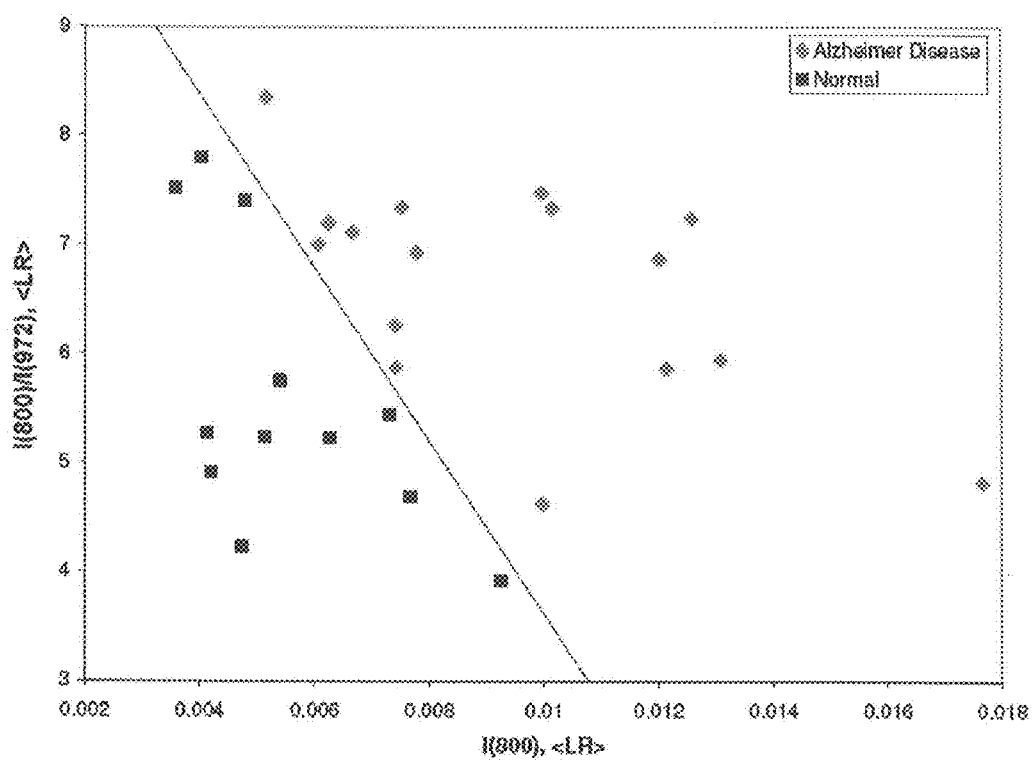
FIG. 6. Plot of intensity at 800 nm (I800) versus the ratio of intensities at 800 nm and 972 nm (I800/I972). The points plotted in the figure represent individual subjects in a study of age matched subjects. If a subject's numerical measure falls below the plotted line, the patient was spectroscopically diagnosed as normal. If a subject's numerical measure lies above the plotted line, the patient was spectroscopically diagnosed as having AD. Subjects clinically diagnosed as normal are indicated by a diamond and subjects clinically diagnosed as having AD are indicated by a square. As shown in the plot, spectroscopic diagnosis correlated with clinical diagnosis of normal or AD, as described in Example 3, infra.

For the data shown in FIG. 6, the cut-off line is $$y = -760x + 11.25$$

Substituting $I_{\lambda(max)}$ for x and ($I_{\lambda(max)}/I_{\lambda(min)}$) for y, the perpendicular distance, D, of each point from the cut off line is given by $$D = I_{\lambda(max)}(1) + (I_{\lambda(max)}/I_{\lambda(min)})(0.0013) - 0.0148$$

When the values for $I_{\lambda(max)}$ and ($I_{\lambda(max)}/I_{\lambda(min)}$) from a patient's spectroscopic measurement are substituted into the above equation and solved for a numerical value of D, D>0, (positive for AD);

D<0, (negative for AD).

Additional means for assigning a numerical value to the spectral profile may be found in the examples.

The brain disease may be associated with abnormal accumulation or deposits of proteins or other molecules or brain injury. For example, the brain disease can be, but is not limited to, one of the following: MCI, AD, Parkinson disease, Lewy Body Dementia, Fronto-temporal Dementia with Lewy Bodies, Pick's Disease, dementia related to alcoholism or exposure to heavy metals (e.g., arsenic, antimony, bismuth), dementia related to infectious diseases (e.g., by viruses (HIV, viral encephalitis), spirochetes (Lyme disease, syphilis) or prions (CJD)), brain injury, other neurodegenerative diseases, diffuse or mild traumatic brain injury (TBI), multi-infarct dementia (MID) (also known as vascular dementia); subdural hematoma; hemorrhage; hydrocephalus.

The abnormal accumulation or deposits of proteins or other molecules associated with brain damage, alters the reflectance, absorbance, transmission, emission and/or scattering of the light passing through the affected brain tissue. For example, the abnormal accumulation or deposits of proteins or other molecules have resulted in the formation of cortical neuritic plaques and/or neurofibrillary tangles that, in turn, alter light reflectance spectra.

In one embodiment of the invention, the subject is human; in another embodiment of the invention, the subject is a mammal, e.g., a dog, cat, cow, or pig.

In another embodiment of the invention, the method may be used to evaluate the stage or severity of the brain disease or injury. In yet another embodiment of the invention, the method is applied repeatedly to monitor the course of the subject's disease, and/or to evaluate the response of the subject to treatment, and/or to determine future treatment of the subject. There is great benefit to early detection of brain damage because early detection permits earlier therapeutic intervention to the subject which may delay or alleviate the onset of more severe brain damage. For example, it is well established that MCI is a prognosticator for early stage AD (P. Fischer, et al. 2007). Accordingly, early detection of MCI may delay the onset of AD provided appropriate therapy can be given to the subject.

In another embodiment of the invention, a fiber optic assembly delivers the light from the light source to the subject's head. In yet another embodiment of the invention, a fiber optic assembly is used to collect light.

Devices of the Invention

The present invention further relates to a device for detecting or evaluating brain damage, such as a brain disease or a brain injury, in a subject. The device comprises: 1) a light source, 2) light delivery and collection optics, 3) a spectrograph, and 4) a light detector.

In one embodiment, the light source is a xenon lamp, a mercury lamp, a tungsten lamp or a laser or any combination of these.

In one embodiment, the light delivery and collection optics is a fiber optic assembly with multiple optical fibers. The optical fibers are positioned upon a subject's head at fixed distances between the fiber optic ends. In a further embodiment, optical fibers are positioned in a headpiece with fixed distances between the fiber optic ends.

In one embodiment, the spectrograph is an f/1.4 or f/1.8 holographic imaging spectrograph with a grating. The grating can be a kinematically exchangeable volume-phase holographic transmission grating, a ruled grating or solid state on-chip grating.

In one embodiment, the light detector is a computer controlled, thermo-electrically cooled charge coupled device (CCD).

Advantages of the Invention

Currently, there is no non-invasive in vivo brain imaging technique that is capable of detecting or evaluating AD in a subject. Definitive diagnosis of AD subjects must wait for post mortem histological evaluation. A light scattering technique may be helpful in detecting plaques and tangles without sections, stains or markers as is the current practice, to determine AD due to the inherent properties of plaques and tangles The disclosure herein provides spectroscopic devices and methods for detecting brain damage from disease, such as AD, non-invasively, in vivo.

Previously published disclosures regarding spectroscopic devices to detect AD (e.g., Hanlon et al., 2004), did not provide devices and methods of the invention that could differentiate AD from non-AD subjects in vivo. Hanlon 2004 disclosed the wavelength dependent distribution of intensity between spectra, i.e., interspectrum wavelength dependent relative intensity but not intraspectrum wavelength dependent relative intensity. The present invention provides that the intensity and relative intensity ratio of the spectra derived from brain damaged subjects and control subjects have a significant difference (e.g., a statistically significant difference).

The devices and the methods of the invention also provide for earlier detection and diagnosis of brain damage, because they permit for example, detection of small differences in brain structure due to brain damage allowing for earlier medical intervention in subjects diagnosed with brain damage.

The following examples are presented to illustrate the present invention and to assist one of ordinary skill in making and using the same. The examples are not intended in any way to otherwise limit the scope of the invention.

Example 1

This example shows data demonstrating the use of near-infrared spectroscopy to detect brain disease (specifically, Alzheimer's disease) in vitro. The methods are described by Hanlon et al., in Optics Letter, 2008, 33(6):624-626, herein incorporated-by-reference in its entirety.

Methods

Samples for thin tissue measurements of transmission and reflectance were prepared from unstained, unfixed, postmortem, temporal pole specimens from human brains, either confirmed to had been affected by Alzheimer's Disease (AD), or as controls (non-AD), which had been flash frozen at autopsy. One temporal pole from each of 2 AD and 2 non-AD brains was used. All cases were neuropathologically confirmed as AD or non-AD control. Each of the two AD cases was late stage AD, one corresponding to Braak stage V and one to Braak stage VI [Braak et al., 2005]. The specimens were partially thawed to obtain microtomed sections approximately 1 mm thick. Fully thawed tissue samples were mounted in optical cells with 1 mm path length and 0.15 mm window thickness. The tissue fully contacted the optical cell windows but was not compressed in the cell. Optical cells were mounted in the integrating sphere of a Cary 5 spectrometer (Varian, Inc., Palo Alto, Calif.). For reflectance measurements, the geometry to reject specular reflection of the incident beam was used. Total integrated reflectance and transmission spectra were acquired over the wavelength range 470 nm-1000 nm. Elapsed time from tissue sectioning to completion of data acquisition was less than four hours.

Unfixed, unstained specimens for gross tissue diffuse reflectance measurements were intact temporal poles, which had been flash frozen at autopsy. One temporal pole from each of 5 AD and 5 non-AD brains was used. All cases were neuropathologically confirmed as AD or non-AD control. Each temporal pole was several cubic centimeters in volume. Immediately prior to measurement, each specimen was brought to room temperature and placed on a microscope cover slip that fully supported it. Incident light from a water-filtered Xe arc source, coupled into the central fiber optic of a low —OH fiber bundle, was delivered to the air-exposed surface of the tissue from a distance of 10 mm, providing a spot size of 15 mm². The incident angle was 30°, to minimize the specular component of the detected reflectance signal. The cover slip was mounted to provide a free path to a mirror positioned about twenty centimeters below, which had been oriented to divert light that had propagated through the sample and cover slip from possible back-reflection into the signal detection fibers. Six detection fibers were arranged around the delivery fiber concentrically, in a close-packed arrangement; all fibers were 200 μm core, NA=0.22. The proximal termination of the detection fibers was a linear array which was positioned at the 100 μm entrance slit of an Acton Spectra-Pro 150 spectrograph (Princeton Instruments Inc., Acton, Mass.) coupled to an Andor DU 434 FI CCD (Andor Technology, Belfast, Northern Ireland), TE cooled to −60° C.

Results

FIG. 1 shows a set of transmission (T) and reflectance (R) spectra for 1 mm thick tissue slabs of one AD specimen (red) and one non-AD control specimen (black). To describe light propagation in the brain tissue slabs, the two flux model implicitly derived from the radiative transport equation [Zede et al., 1991] was modified as follows. The resulting equations, used to describe the tissue reflectance, R and transmission, T in terms of the absorption coefficient ($\mu_a$) and reduced scattering coefficient ($\mu_s'$) are presented in Equations (1) and (2):

$$R = \frac{1-r^2}{r} C \quad (1)$$

$$T = \left[C - \frac{r\Lambda}{2(1-r)(1+\gamma)}(1 - \exp[-1(1+\lambda)\tau])\right]\exp(\gamma\tau) + \quad (2)$$
$$\left[-C + \frac{\Lambda}{2(1-r)(1+\gamma)}(1 - \exp[-1(1-\lambda)\tau])\right]\exp(-\gamma\tau)$$

where, $$C = \frac{r\Lambda}{2(1-r)(1+\gamma)(1-r^2\exp(-2\gamma\tau))}$$
$$\left[1 - r\frac{1+\gamma}{1-\gamma}\exp(-2\gamma\tau) + \left(r\frac{1+\gamma}{1-\gamma} - 1\right)\exp[-(1+\gamma)\tau]\right],$$
$$r = \frac{a(1-\Lambda)-\gamma}{b\Lambda} - 1,$$
$$\gamma = a[(1-\Lambda)(1-\Lambda+2b/a\Lambda)]^{1/2},$$
$$\Lambda = \frac{\mu_s'}{\mu_a + \mu_s'},$$
and
$$\tau = (\mu_a + \mu_s')L,$$

where L is the tissue thickness.

Figure 2:
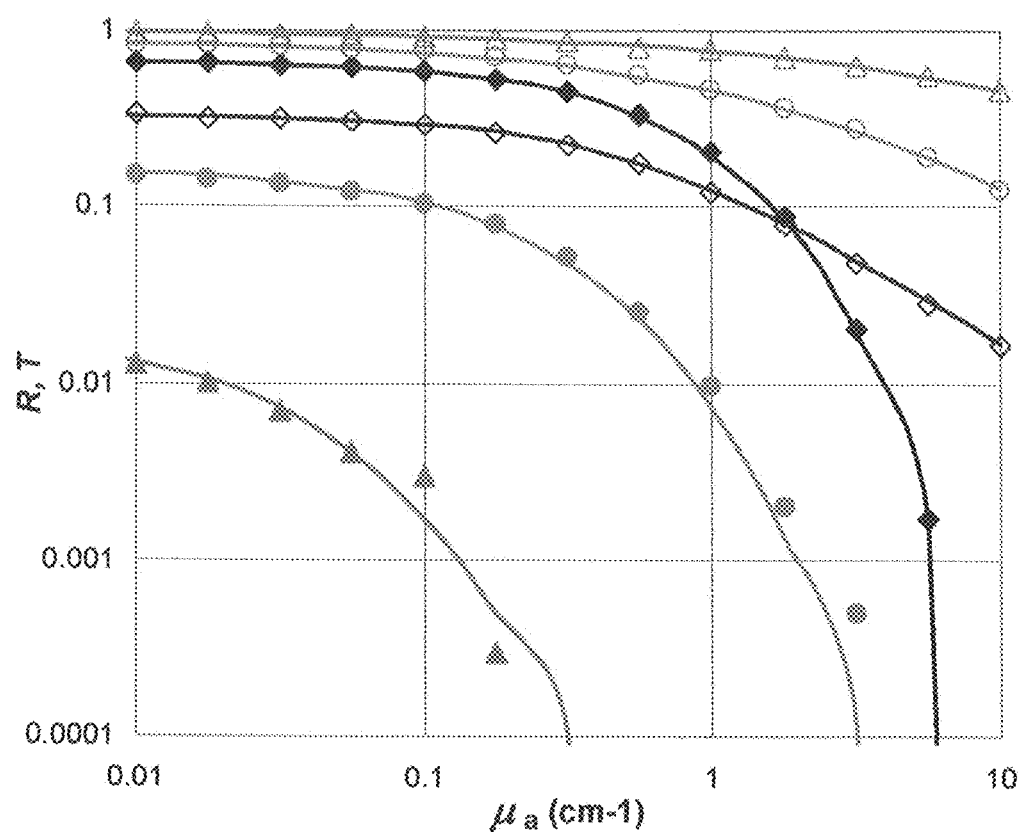
FIG. 2. Reflectance and transmission (R, T) calculated for a turbid slab of 1 mm thickness using Eqs. 1 and 2 (solid line) and Monte Carlo simulations (symbols) over a range of $0.01 \leq \mu_a \leq 10.0$ (cm$^{-1}$) and $1 \leq \mu_s' \leq 100$ (cm$^{-1}$). Open symbols indicate reflectance, solid symbols indicate transmission. Triangle symbols indicate R, T with $\mu_s'=1$ cm$^{-1}$, circles indicate R, T with $\mu_s'=10$ cm$^{-1}$ and diamonds indicate R, T with $\mu_s'=100$ cm$^{-1}$, as described in Example 1, infra.
Figure 3:
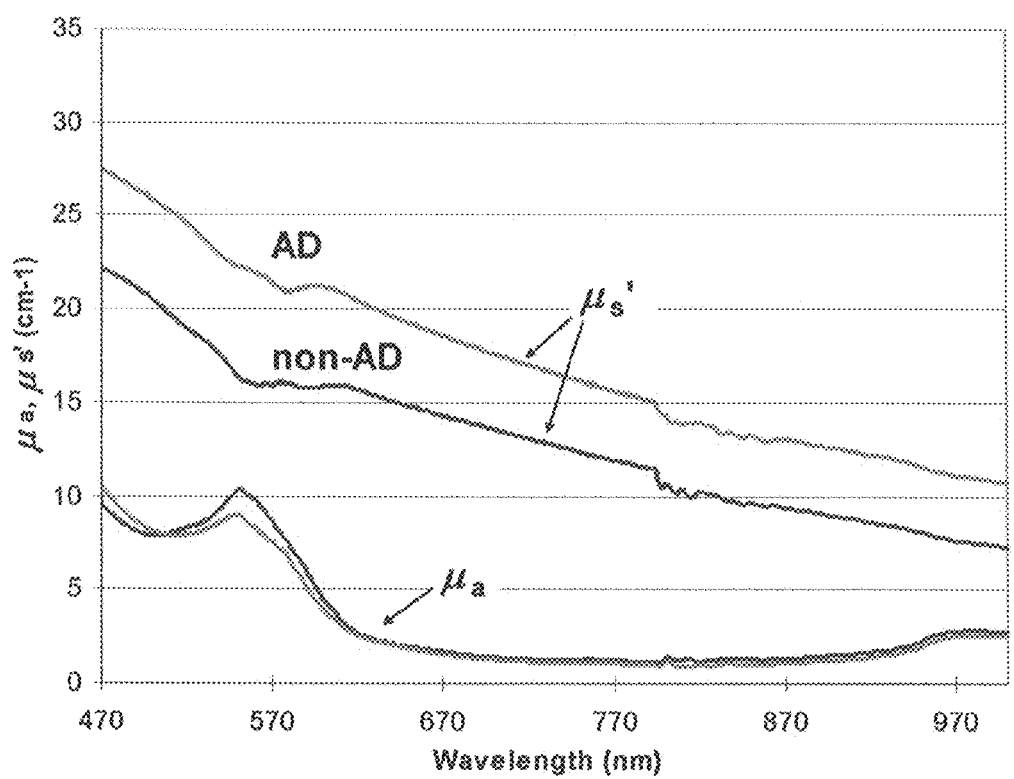
FIG. 3. Absorption ($\mu_a$) and reduced scattering ($\mu_s'$) coefficients for non-AD and AD brain samples obtained by fitting Eqs. 1 and 2 (see Example 1), to the experimental spectra (FIG. 1), as described in Example 1, infra.

To apply this model to the observed reflectance and transmission spectra requires evaluation of the parameters, a and b, which include the effects of the phase function and boundary conditions. These two parameters were determined by fitting the reflectance and transmission modeled by Eqs. (1) and (2) to Monte Carlo simulations. FIG. 2 shows the fit of modeled reflectance and transmission to Monte Carlo simulations for a=1.859 and b=0.5536, over a range covering biomedically relevant values for $\mu_a$ and $\mu_s'$. Using these values for a and b, the values of $\mu_a$ and $\mu_s'$ were determined that gave the best fit of the model to the observed reflectance and transmission spectra, FIG. 3. FIG. 3 presents the wavelength dependent optical constants for AD brain tissue and normal brain tissue over the wavelength range 470-100 nm, which are consistent with prior reports at single or a few wavelengths [Van der Zee et al., 1993; Cheong et al., 1990].

As shown in FIG. 3, scattering shows a significant difference between AD and non-AD tissue, while absorption, dominated by hemoglobin, provides less distinction. More importantly, the slope of the wavelength dependent reduced scattering coefficient for AD brain is very distinct from that of the non-AD control.

Figure 4:
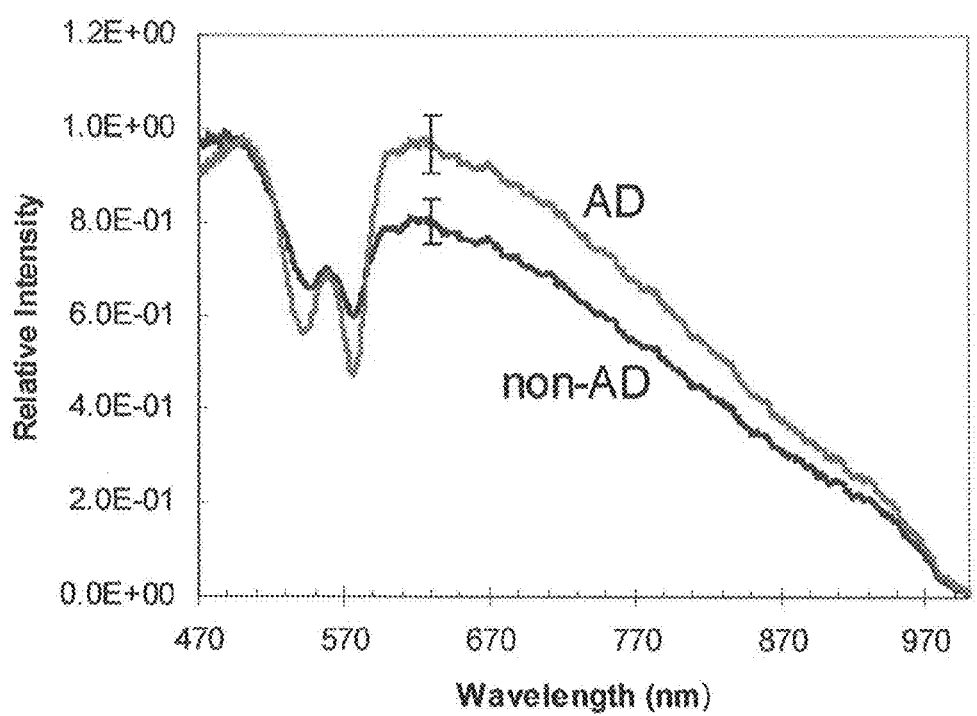
FIG. 4. Mean diffuse reflectance spectra of five intact temporal pole specimens from five different, neuropathologically confirmed Alzheimer disease cases (AD) and five different, neuropathologically confirmed neurological control cases (non-AD). Error bars indicate the standard error of the mean for the AD and non-AD populations based on the five spectra measured for each group, as described in Example 1, infra.

FIG. 4 shows mean diffuse reflectance spectra of the intact temporal pole specimens from AD and non-AD control cases. Each mean spectrum is the average five spectra (one spectrum per specimen), for each diagnosis. The diffuse reflectance spectra confirm that scattering and slope, particularly in the range 670-970 nm, where there is little absorption, clearly differentiate AD brain tissue from non-AD control brain tissue.

Discussion

The increased scattering observed for AD brain tissue compared to control brain tissue in this Example, is consistent with the histopathologic changes known to occur in AD, in the form of NP and NFT. Both NP and NFT are dense protein aggregates whose characteristic physical chemical properties are distinct from surrounding tissue. As such, NP and NFT should behave as small light scattering particles that contribute to the reported differences between diseased and non-diseased brain tissue. The presence of NP and NFT should increase light scattering in AD brain. Furthermore, the characteristic sizes of NP and NFT, several tens of microns, would be expected to contribute to an increase in the long-wavelength slope of the scattering spectrum, because they are large scatterers compared to the surrounding tissue compartments (nuclei, organelles, etc.) [Perelman et al., 1998]. This again is consistent with the increase in slope observed for AD compared to non-AD brain tissue in the 670-970 nm region of the reported spectra.

Near infrared (NIR) light propagates harmlessly through the overlying tissue, bone and cerebrospinal fluid to probe the brain non-invasively. Histological features in the AD damaged brain, such as NP and NFT are dense protein aggregates distinct from normal histology, which should provide characteristic light scattering signatures. These and other features of AD pathology may also contribute distinct NIR fluorescence [Hanlon, 1999] and absorption spectra as well. Thus, a direct connection between the inherent optical properties of brain tissue and the known neuropathological features of AD and related neurodegenerative diseases can be provided, without the need for exogenous markers, by NIR optical spectroscopy.

Example 2

This example shows data demonstrating the use of near-infrared spectroscopy to detect brain disease in vivo.

Methods

Spectra were acquired from two male human subjects, ages 78 and 83 years, who met the NINCDS-ADRDA criteria for probable AD, and two male, community dwelling control subjects, ages 68 and 75. Informed consent was obtained as approved by the Bedford VA Medical Center IRB; procedures conformed to the Declaration of Helsinki Neuropathologic confirmation of AD was subsequently obtained for both probable AD subjects.

An NIR spectrometer device which was a prior implementation of the current invention, consisting of four components, described in detail below in this example, was used to acquire spectroscopic data on the subjects with and without probable AD. Spectra were collected over the range of 486-1037 nm, and data in the region of about 610-1030 nm acquired with this device were found to be useful for this analysis. The light intensities were recorded approximately every 0.4 nm in this range. A fiber optic assembly delivered light from a xenon arc lamp onto the subject's temple and collected diffusely reflected light, which was detected using a cooled CCD (charge coupled device) interfaced to an imaging spectrograph. One series of measurements was made on each temple of each subject, with different distances of 15, 20, 22.5, 25, 27.5 and 30 mm separating the placement of collection and delivery fibers (source-detector separation) for each measurement in a series.

1. Light Source

The broadband light source was a Xe (xenon) small-arc lamp (Newport Corp., Irvine, Calif.), including water filter, with output over a wavelength range similar to the current device.

2. Light Delivery and Collection Optics Component

The light delivery optical train consists of the fiber optic used to deliver light from the sources to the surface of the subject's head and coupling optics, positioned between the source and the delivery fiber. The delivery fiber optic is a single flex-cabled, 600 μm (micrometer) core, silica fiber 3 m (meter) in length with standard SMA (Sub-Miniature A) connectors at both ends (for example, such as those available from Amphenol Corporation, 358 Hall Avenue, Wallingford, Conn. 06492).

The light collection fiber optic was constructed of a bundle of 37 polyimide jacketed, 200 μm core, low —OH, silica fibers cleaved from a single strand (Fiberguide Industries, Inc., Stirling, N.J.) into 3 m lengths. The polyimide jacket is stripped from one end of each of the 3 m lengths. The stripped ends of these fibers are assembled into a concentric, close-packed array and potted in optical epoxy (Epoxy Technology, Billerica, Mass.) and encapsulated in heat shrink tubing and polished, forming the distal end of the collection fiber. Approximately 1 m from the proximal end, the collection fiber optic is trifurcated. The proximal ends of the 18 fibers comprising the inner (6 fibers) and middle (12 fibers) rings of the distal concentric array are assembled into a linear array and potted in optical epoxy and encapsulated in an aluminum tube and polished. The proximal ends of the 18 fibers comprising the outer ring of the distal concentric array are assembled into a linear array and potted in optical epoxy and encapsulated in an aluminum tube and polished. Each proximal end linear array of the collection fiber optic can be positioned at the focal plane of the entrance slit of the dispersion stage spectrograph. The proximal end of the center fiber of the distal concentric array is terminated in a standard SMA connector and polished. The entire length of the collection fiber optic is jacketed in flexible acrylate tubing with flex-strain relief at all ends and epoxy reinforcement at the trifurcation point.

The distal ends of the light delivery and collection optics are positioned upon the subject's head using a hard plastic template held in place manually to maintain the delivery and collection fiber optics at fixed distances of separation between them, (source-collection distance, scd) of 15, 20, 22.5, 25, 27.5 and 30 mm.

3. Imaging Spectrograph Component

The dispersion/filtering stage consisted of an f/1.4 imaging spectrograph with rotating, turret mounted, ruled grating blazed at 600 nm providing a range of approximately 486-1037 nm when rotated to a center wavelength of approximately 760 nm. (Princeton Instruments, Acton Research Corp., Acton, Mass.).

4. Detector

The detector was a computer controlled, thermo-electrically cooled, front illuminated CCD with 1024×1024 pixels, each 13×13 μm in area (Andor Technology, LLC., Belfast, Northern Ireland).

Using the device and parameters described in this example, two types of data were acquired: reference data and patient data.

Reference Data

The delivery and collection fiber optics were targeted to a 1 cm deep barium sulfate powder in an open 9.5 cm diameter Petri dish, in a manner to minimize edge effects and specular reflectance entering the collection fiber optic. The source shutter was opened and data acquisition was initiated for a period of time (exposure time) by entering a computer command. The source shutter was then closed and data acquisition was initiated for an equal exposure time by entering a computer command. The exposure time for the reference spectrum data was chosen to maximize the signal to noise ratio (S/N) while maintaining the detected signal level within the linear operating range of the detector as described above.

Patient Data

Data were acquired at each scd. The template was applied to the patient's head so that it was positioned at the temple, approximately over the pole of the temporal lobe of the brain. The distal end of the delivery fiber optic was inserted into the first template penetration posterior and the distal end of the collection fiber optic was inserted into the second template penetration posterior. The source shutter was opened and data acquisition was initiated for a period of time (exposure time) by entering a computer command. The source shutter was closed and data acquisition was initiated for an equal exposure time by entering a computer command. As for the reference data, the exposure time target was that which maximized S/N while maintaining a linear signal as described above. The collection fiber optic was removed then inserted into the third template penetration posterior. The source shutter was opened, etc.; this was repeated for each scd, first on one temple then the other, for each patient.

Data Analysis

The reference and patient data acquired by the device in this example were analyzed as follows.

The "shutter closed" data ($S_A$) was subtracted from the corresponding "shutter opened" data ($S_L$) for each acquisition of each type of data (reference and patient), for each fiber in the collection fiber bundle individually $$S_A = A(\lambda)r(\lambda)D(\lambda)t$$

$$S_L = [I_0(\lambda) + A(\lambda)]r(\lambda)D(\lambda)t,$$

where $I_0(\lambda)$ was the source light intensity incident on the target, $A(\lambda)$ was the ambient light intensity incident on the target, $r(\lambda)$ was the reflectance of the target, $D(\lambda)$ was the detector response function and t was the total exposure time, producing a background corrected (c) reference (R) spectrum for each fiber in the collection fiber bundle individually $$^cS_R(\lambda) = I_0(\lambda) r_R(\lambda) D(\lambda) t_R,$$

and a background corrected patient spectrum for each fiber in the collection fiber bundle individually at each scd (i), on each temple (l, d) of each patient (P).

$$^{l,d,c}S_P^i(\lambda) = I_0(\lambda)^{l,d} r_P^i(\lambda) D(\lambda)_s^{l,d} t_P^i.$$

In this example, one embodiment of the method of analysis was used wherein the background corrected patient spectra for each fiber in the collection fiber bundle individually were divided by the corresponding reference spectra for each fiber in the collection fiber bundle individually, producing the ratioed patient spectrum, $_jS_P$ for the $j^{th}$ collection fiber.

$$_jS_P = {_j^c}S_P / {_j^c}S_R,$$

where the indices l, d, and i have been dropped to simplify notation. The $_jS_P$ are summed and normalized to unit intensity at 730 nm $$\sum_j {_jS_P} / I_{\lambda(730)} = {}^NS_P$$

Figure 5:
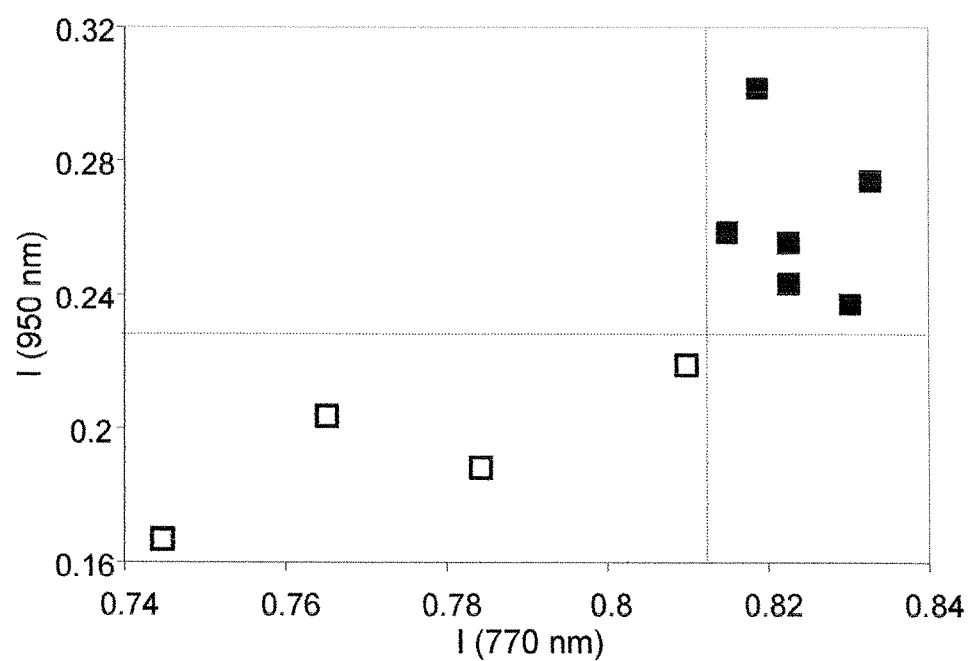
FIG. 5. Plot of intensity at 950 nm versus intensity at 770 nm for each normalized spectrum acquired in vivo. Each spectrum represented in the figure was measured with the same distance separating delivery and collection fibers on each temple of each subject. Open squares are AD subjects; closed squares are control subjects; as described in Example 2, infra.

The normalized intensities of $^NS_P^i$ at λ=950 nm and λ=770 nm for i=25 mm are plotted in FIG. 5, demonstrating differentiation of AD (empty square) and control (black square).

Using this embodiment of the method, these properties of $S_P$ were used in a study of AD to assign a numerical measure to each patient based on his absorbance, transmission and reflectance spectrum. The numerical measure thus determined was used to assign a spectroscopic diagnosis for each patient.

This connection between $S_P$ and diagnosis is the basis for relating the measured patient spectrum ($S_P$) to diagnosis with respect to AD, related neurodegenerative disorders and/or brain injury.

Results

Diffuse reflectance spectra are characterized by mean intensity and spectroscopic lineshape (the wavelength dependent distribution of intensity within each spectrum). This example demonstrates that the mean intensity of AD subjects' spectra was greater than that of controls' spectra by 40%, (p<0.001; t-test). To compare spectroscopic lineshapes, spectra were normalized to unit intensity at 730 nm (thus removing mean intensity as a factor) and the relative intensities at 950 nm and 770 nm for each spectrum measured at one source-detector separation were plotted. FIG. 5 shows AD subjects are clearly differentiated from control subjects (p=0.017; t-test; Fisher's linear discriminant).

Discussion

Near-infrared light collected at different source-detector separations has traversed different depths of tissue [Okada et al., 1997]. At the source-detector separation of the reported spectra, the effective light path traverses the lateral temporal cortex [Okada et al., 1997], a site of early neuropathological involvement in AD [Morris et al., 2001]. As near-infrared light propagates through the tissue, it can be scattered or absorbed. In vitro measurements show scattering is the dominant distinction between AD and control brains [Hanlon et al., 2008]. In AD brains, cortical plaques and tangles increase the scattering coefficient and change the spectroscopic lineshape [Hanlon et al., 2008]. The increased scattering coefficient should contribute to increased diffuse reflectance for AD subjects, as was observed. Also, cortical atrophy of AD increases the relative proportion of cerebrospinal fluid, which functions optically as a light guide [Hanlon et al., 1999], conveying more light to larger source-detector separations. As shown in this example, the effect of scattering on lineshape, which is observed in vitro, also is seen in vivo. Scattering dominates (absorption is weak) over the range 770 to 950 nm in the reported spectra. FIG. 5 shows the significant difference in spectroscopic lineshape observed over this wavelength range between AD and control subjects' spectra.

This is the first demonstration that near-infrared spectroscopy can distinguish normal brain from AD brain in vivo. AD pathology can be observed through the changes in light transmission through the human brain in the near-infrared optical window. In comparison to magnetic resonance and positron emission imaging techniques, near-infrared spectroscopy is inexpensive and non-invasive. Therefore, this approach has use as a screening method for asymptomatic individuals with brain damage, or as a tool for monitoring the effects of therapeutics.

Example 3

This example shows data demonstrating the use of near-infrared spectroscopy to detect brain disease in vivo.

Methods

Spectra on age matched human subjects at the Edith Nourse Rogers Memorial Veterans Hospital were acquired as follows. Twelve subjects were clinically diagnosed as normal i.e. did not have AD. Fifteen subjects were clinically diagnosed with AD.

A device comprising four components, described in detail below, was used to acquire spectra data on the subjects with and without probable AD. Spectra from a range of about 610-1030 nm was acquired with a NIR spectrometer.

1. Light Source and Dispersion Component

The light sources provide broadband illumination from 250 nm (nanometers) to >2400 nm. The light sources were a 50 W (Watt), continuous wave, Hg (mercury) small-arc lamp (Newport Corp., Irvine, Calif.) and a 6.5 W tungsten filament halogen lamp (Ocean Optics, Inc., Dunedin, Fla.). The Hg source included a water filter which limited available light from this source to the wavelengths between approximately 400 and 1000 nm. Both sources incorporated a shutter.

2. Light Delivery and Collection Optics Component

The light delivery optical train consists of the fiber optic used to deliver light from the sources to the surface of the patient's head and coupling optics, positioned between the source and the delivery fiber. For the Hg source, the coupling optics were designed to maximize the efficiency with which light from the source is directed into the delivery fiber optic, using lenses (Newport Corp., Irvine, Calif.) to meet design requirements. For the tungsten halogen source, the coupling optics were included in its (manufacturer supplied) housing and are not designed for coupling into a specified fiber optic. The delivery fiber optic is a single, acrylate jacketed, flex-cabled, 600 μm (micrometer) core, low —OH (hydroxyl content), silica fiber 3 m (meter) in length with a high-power SMA (Sub-Miniature A) connector at the light source (proximal) end and a standard SMA connector at the patient (distal) end. (The delivery fiber was manufactured according to stated requirements and specifications by Polymicro Technologies (Phoenix, Ariz.) or Molex, Inc. (Downers Grove, Ill.).

The light collection fiber optic consisted of a bundle of 37 polyimide jacketed, 200 μm core, low —OH, silica fibers cleaved from a single strand (Fiberguide Industries, Inc., Stirling, N.J.) into 3 m lengths. The polyimide jacket was stripped from one end of each of the 3 m lengths. The stripped ends of these fibers were assembled into a concentric, close-packed array and potted in optical epoxy (Epoxy Technology, Billerica, Mass.) and encapsulated in heat shrink tubing and polished, forming the distal end of the collection fiber. Approximately 1 m from the proximal end, the collection fiber optic was trifurcated. The proximal ends of the 18 fibers comprising the inner (6 fibers) and middle (12 fibers) rings of the distal concentric array were assembled into a linear array and potted in optical epoxy and encapsulated in an aluminum tube and polished. The proximal ends of the 18 fibers comprising the outer ring of the distal concentric array were assembled into a linear array and potted in optical epoxy and encapsulated in an aluminum tube and polished. Each proximal end linear array of the collection fiber optic can be positioned at the focal plane of the entrance slit of the dispersion stage spectrograph. The proximal end of the center fiber of the distal concentric array was terminated in a standard SMA connector and polished. The entire length of the collection fiber optic was jacketed in flexible acrylate tubing with flex-strain relief at all ends and epoxy reinforcement at the trifurcation point. The entire collection fiber assembly was encased in a black spiral-cut sheath, except for the last, approximately 6 cm (centimeters) of each end.

The distal ends of the light delivery and collection optics were positioned upon the patient's head using an elasticized headband, which incorporates a hard plastic template. The template provides for accurate and reproducible positioning of the delivery and collection fiber optics at fixed distances of separation between them, (source-collection distance, scd) of 10, 15, 20, 25 and 30 mm.

3. Imaging Spectrograph Component

The dispersion/filtering stage consists of an f/1.8 holographic imaging spectrograph with a kinematically exchangeable volume-phase holographic transmission grating providing a 400 nm range centered at 850 nm (Kaiser Optical Systems, Inc., Ann Arbor Mich.).

4. Detector

The detector is a computer controlled, thermo-electrically cooled, open-electrode CCD (charge coupled device)[again define this above when term is first used] with 256×1024 pixels, each 25×25 μm in area (Andor Technology, LLC, Belfast, Northern Ireland).

Data Acquisition Routine to Maximize the Signal to Noise Ratio (S/N) within CCD Dynamic Range The first step in the data acquisition sequence, which is controlled by the data acquisition program of the current invention, is a preliminary acquisition made to estimate the single-exposure time (exp) required to maximize the signal-to-noise ratio (S/N) within the linear dynamic range of the detector (about 50000 counts for the CCD of the current invention operated at a gain corresponding to the read-rate of 16 microseconds):

The parameter denoting the preliminary acquisition time is "acq" (0.021 seconds, the minimum achievable at the CCD operating conditions described). The maximum value (counts) of the preliminary spectrum is determined and stored in the variable "max." At the wavelength of max:

$$max = (Isig \times acq) + (Ibkg \times acq)$$

where $Isig$=the signal intensity, in counts/second $Ibkg$=the background intensity, in counts/second $Ibkg$ is not expected to change from one scd to another or from time to time during a single measurement sequence. An examination of the data shows that this is the case. To avoid making background measurements with each preliminary acquisition, $Ibkg$ is initially taken as 400 (typical for the measurement conditions at the minimum achievable exposure time for the CCD operating conditions, described above). Hence, $$max = Isig \ast acq + 400 \ast acq$$

or $$max/acq - 400 = Isig$$

Exposure time for the first actual data acquisition, at 10 mm scd, is set at exp=50000/Isig, yielding a peak signal intensity of ~50000 counts.

After the 10 mm spectrum is acquired, acq is reset to the exposure time of the 10 mm spectrum, $acq_{(10\ mm)}$ and $Ibkg$=400 is replaced by the actual background data acquired for the 10 mm measurement, $Ibkg_{(10\ mm)}$. Using these values, exp is recalculated as above from a preliminary acquisition for each subsequent measurement yielding actual data acquisition For each measurement, the program executes the following sequence:

1. Execute a preliminary acquisition with integration time=acq and estimate exp as above.
2. Record the CCD operating conditions in log file.
3. Acquire a spectrum with the estimated exposure time (raw).
4. Acquire a background spectrum with same exposure time (bkg).
5. Calculate and store diff spectrum: raw-bkg.
6. Calculate and store cor spectrum: diff/ref.
7. Calculate and store tcor spectrum: cor/exp.

The data acquisition routine described in this example is an improvement over the trial and error method used in Example 2 to maximize S/N in the measurements. This improvement allows shortened total examination time per patient.

Using the device and parameters described in this example, two types of data were acquired: reference data and patient data.

Reference Data

For each source separately, the delivery and collection fiber optics were targeted to a Spectralon® diffuse reflectance standard (Labsphere, Inc., North Sutton, N.H.) in a manner to minimize specular reflectance entering the collection fiber optic. The source shutter was opened and data acquisition was initiated for a period of time (exposure time) by entering a computer command. The source shutter was then closed and data acquisition was initiated for an equal exposure time by entering a computer command. The exposure time for the reference spectrum data was chosen to maximize the signal to noise ratio (S/N) while maintaining the detected signal level within the linear operating range of the detector, as described in Example 2.

Patient Data

For each source separately, data are acquired at each scd. The elasticized headband was applied to the patient's head so that the template is positioned at the temple, approximately over the pole of the temporal lobe of the brain. The distal end of the delivery fiber optic was inserted into the first template penetration anterior and the distal end of the collection fiber optic was inserted into the second template penetration anterior. The source shutter was opened and data acquisition was initiated for a period of time (exposure time) by entering a computer command. The source shutter was closed and data acquisition was initiated for an equal exposure time by entering a computer command. As for the reference data, the exposure time target was that which maximized S/N while maintaining a linear signal as described in Example 2. Since there was inter-patient variability in the level of the detected signal at each scd, and since there was variability in the level of the detected signal at each scd for each patient, the exposure time was calculated and controlled by software developed for this purpose. The collection fiber optic was removed then inserted into the third template penetration anterior. The source shutter was opened, etc.; this was repeated for each scd, first on one temple then the other, for each patient.

Data Analysis

The reference and patient data acquired by the device in this example were analyzed as follows.

The "shutter closed" data ($S_A$) was subtracted from the corresponding "shutter opened" data ($S_L$) for each acquisition of each type of data (reference and patient), $$S_A = A(\lambda) r(\lambda) D(\lambda) t$$

$$S_L = [I_0(\lambda) + A(\lambda)] r(\lambda) D(\lambda) t,$$

where $I_0(\lambda)$ is the source light intensity incident on the target, $A(\lambda)$ is the ambient light intensity incident on the target, $r(\lambda)$ is the reflectance of the target, $D(\lambda)$ is the detector response function and t is the total exposure time, producing a background corrected (c) reference (R) spectrum for each source (s)

$$_s^c S_R(\lambda) = {}^s I_0(\lambda) r_R(\lambda) D(\lambda) t_R,$$

and a background corrected patient spectrum for each source, at each scd (i), on each temple (l, d) of each patient (P).

$$_s^{l,d,c} S_P^i(\lambda) = {}^s I_0(\lambda)^{l,d} r_P^i(\lambda) D(\lambda) {}_s^{l,d} t_P^i.$$

In one embodiment of the method of analysis, the reference spectra for each source were normalized to unit integrated intensity, yielding the normalized reference spectra, $^N S_R(\lambda)$ $$^N S_R(\lambda) = {}^c S_R(\lambda) / t_R \int {}^c S_R(\lambda) d\lambda$$
$$= \frac{I_0(\lambda) r_R(\lambda) D(\lambda) t_R}{\int {}^c S_R(\lambda) d\lambda \cdot t_R},$$

where the indices l, d, s and i have been dropped to simplify notation. The intensities of the background corrected patient spectra were rectified for exposure time, $$_s^{l,d,t} S_P^i = {}_s^{l,d,c} S_P^i / {}_s^{l,d} t_P^i.$$

The diagnostic patient spectrum, $S_P$, is $$S_P = {}^t S_P / {}^N S_R$$
$$= I_0(\lambda) r_P(\lambda) D(\lambda) \left[ \frac{I_0(\lambda) r_R(\lambda) D(\lambda)}{\int {}^c S_R(\lambda) d\lambda} \right]^{-1}$$
$$= r_P(\lambda) \cdot \int {}^c S_R(\lambda) d\lambda,$$

where again, the indices l, d, s and i have been dropped to simplify notation.

The coordinates $(I_{\lambda(max)}, I_{\lambda(max)}/I_{\lambda(min)})$ are calculated from $S_P$, $$I_{\lambda(max)} = \langle [I_{\lambda(799.35)}, I_{\lambda(800.99)}] \rangle \text{ and } I_{\lambda(min)} = \langle [I_{\lambda(970.12)}, I_{\lambda(974.88)}] \rangle,$$

where $\langle \rangle$ indicates the average value over the interval.

A scatter plot of the coordinates $(I_{\lambda(max)}, I_{\lambda(max)}/I_{\lambda(min)})$ differentiates $S_P$ of patients with different diagnoses, establishing $S_P$ as a measure of whether or not the patient has AD, a related neurodegenerative disorder or traumatic brain injury.

Using this embodiment of the method, these properties of $S_P$ were used in a study of AD to assign a numerical measure to each patient based on his spectrum. The numerical measure thus determined was used to assign a spectroscopic diagnosis for each patient. The numerical measures were determined from the intensity at the wavelength of maximum intensity ($I_{\lambda(max)}$, above) for each $S_P$ of each patient at each scd, and the ratio of the intensities ($I_{\lambda(max)}/I_{\lambda(min)}$, above) at the wavelength of maximum intensity and the long wavelength minimum, about 970 nm.

This connection between $S_P$ and diagnosis is the basis for various methods of relating the measured patient spectrum ($S_p$) to diagnosis with respect to AD, related neurodegenerative disorders and/or brain injury Results and Discussion An algorithm, in which the data collected in this example can be used, was developed for determining patient diagnosis of AD or non-AD as follows.

If the equation of the cut-off line is in the form, y=mx+b, then for each point in the scatter plot the perpendicular distance, r, from the point (x, y) to the cut-off line is given by the expression $$r = x(-m/\sqrt{m^2+1}) + y(1/\sqrt{m^2+1}) - b/\sqrt{m^2+1}$$

For the data shown in FIG. 6, the cut-off line is $$y = -760x + 11.25$$

Substituting $I_{800}$ for x and $(I_{800}/I_{972})$ for y, the perpendicular distance, D, of each point from the cut off line is given by $$D = I_{800}(1) + (I_{800}/I_{972})(0.0013) - 0.0148$$

When the values for $I_{800}$ and $I_{800}/I_{972}$ from a patient's spectroscopic measurement are substituted into the above equation, D greater than 0 classifies the subject as having Alzheimer's disease (positive for AD) and D less than 0 classifies the subject as normal (negative for AD):

| I800 | I800/I972 | Dx | Clinical Diagnosis |
| --- | --- | --- | --- |
| 0.0176717 | 4.81645 | 0.00913308 | AD |
| 0.00999408 | 4.62354 | 0.00120468 | AD |
| 0.00668299 | 7.11257 | 0.00112933 | AD |
| 0.0121559 | 5.86219 | 0.00497675 | AD |
| 0.0120314 | 6.86731 | 0.0061589 | AD |
| 0.00743596 | 5.86953 | 0.000266349 | AD |
| 0.00742383 | 6.25925 | 0.000760855 | AD |
| 0.0130951 | 5.94407 | 0.00602239 | AD |
| 0.00781126 | 6.92565 | 0.0020146 | AD |
| 0.00998382 | 7.47188 | 0.00489726 | AD |
| 0.00754508 | 7.3407 | 0.00228799 | AD |
| 0.0101689 | 7.33214 | 0.00490068 | AD |
| 0.00627002 | 7.19544 | 0.000824092 | AD |
| 0.0125949 | 7.2401 | 0.00720703 | AD |
| 0.00517301 | 8.35276 | 0.0012316 | AD |
| 0.00609016 | 6.99727 | 0.000386611 | AD |
| 0.00474087 | 4.23064 | −0.0045593 | Normal |
| 0.00414165 | 5.26896 | −0.0038087 | Normal |
| 0.00541107 | 5.75009 | −0.00191381 | Normal |
| 0.00359674 | 7.51958 | −0.00142781 | Normal |
| 0.00480064 | 7.40727 | −0.000369909 | Normal |
| 0.00514067 | 5.23376 | −0.00285544 | Normal |
| 0.00403856 | 7.8018 | −0.0006191 | Normal |
| 0.00925723 | 3.92279 | −0.000443143 | Normal |
| 0.00768457 | 4.69163 | −0.00101631 | Normal |
| 0.00732455 | 5.43783 | −0.000406271 | Normal |
| 0.00420682 | 4.91148 | −0.00420826 | Normal |
| 0.00627817 | 5.22429 | −0.00173025 | Normal |

The points plotted in FIG. 6 represent individual subjects. If a subject's numerical measure fell below the plotted line, the patient was spectroscopically diagnosed as normal. If a subject's numerical measure lies above the plotted line, the patient was spectroscopically diagnosed as having AD. Subjects clinically diagnosed as normal are indicated by square and subjects clinically diagnosed as having AD are indicated by diamond. The scatter plot shows statistically very significant differentiation between AD and control (p=0.0006). Therefore, as shown in the plot, spectroscopic diagnosis correlated with clinical diagnosis of normal or AD.

Example 4

This example shows data demonstrating the use of near-infrared spectroscopy to detect brain disease in vivo.
Methods Spectra on age matched human subjects at the Edith Nourse Rogers Memorial Veterans Hospital were acquired as follows. Nine subjects were clinically diagnosed as normal i.e. did not have AD. Sixteen subjects were clinically diagnosed with AD.

A device comprising four components, described in detail below, was used to acquire spectra data on the subjects with and without probable AD. Spectra from a range of about 610-1030 nm was acquired with a NIR spectrometer.
1. Light Source and Dispersion Component The light sources provide broadband illumination from 250 nm (nanometers) to >2400 nm. The light sources were a 50 W (Watt), continuous wave, Hg (mercury) small-arc lamp (Newport Corp., Irvine, Calif.) and a 6.5 W tungsten filament halogen lamp (Ocean Optics, Inc., Dunedin, Fla.). The Hg source included a water filter which limited available light from this source to the wavelengths between approximately 400 and 1000 nm. Both sources incorporated a shutter.
2. Light Delivery and Collection Optics Component The light delivery optical train consists of the fiber optic used to deliver light from the sources to the surface of the patient's head and coupling optics, positioned between the source and the delivery fiber. For the Hg source, the coupling optics were designed to maximize the efficiency with which light from the source is directed into the delivery fiber optic, using lenses (Newport Corp., Irvine, Calif.) to meet design requirements. For the tungsten halogen source, the coupling optics were included in its (manufacturer supplied) housing and are not designed for coupling into a specified fiber optic. The delivery fiber optic is a single, acrylate jacketed, flex-cabled, 600 µm (micrometer) core, low —OH (hydroxyl content), silica fiber 3 m (meter) in length with a high-power SMA (Sub-Miniature A) connector at the light source (proximal) end and a standard SMA connector at the patient (distal) end. (The delivery fiber was manufactured according to stated requirements and specifications by Polymicro Technologies (Phoenix, Ariz.) or Molex, Inc. (Downers Grove, Ill.).

The light collection fiber optic consisted of a bundle of 37 polyimide jacketed, 200 µm core, low —OH, silica fibers cleaved from a single strand (Fiberguide Industries, Inc., Stirling, N.J.) into 3 m lengths. The polyimide jacket was stripped from one end of each of the 3 m lengths. The stripped ends of these fibers were assembled into a concentric, close-packed array and potted in optical epoxy (Epoxy Technology, Billerica, Mass.) and encapsulated in stainless steel tubing and polished, forming the distal end of the collection fiber. Approximately 1 m from the proximal end, the collection fiber optic was trifurcated. The proximal ends of the 18 fibers comprising the inner (6 fibers) and middle (12 fibers) rings of the distal concentric array were assembled into a linear array and potted in optical epoxy and encapsulated in a stainless steel tube and polished. The proximal ends of the 18 fibers comprising the outer ring of the distal concentric array were assembled into a linear array and potted in optical epoxy and encapsulated in a stainless steel tube and polished. Each proximal end linear array of the collection fiber optic can be positioned at the focal plane of the entrance slit of the dispersion stage spectrograph. The proximal end of the center fiber of the distal concentric array was terminated in a standard SMA connector and polished. The entire length of the collection fiber optic was jacketed in black PVC monocoil with flex-strain relief at all ends and epoxy reinforcement at the trifurcation point. The entire collection fiber assembly was encased in a black PVC monocoil sheath.

The distal ends of the light delivery and collection optics were positioned upon the patient's head using an elasticized headband, which incorporates a hard plastic template. The template provides for accurate and reproducible positioning of the delivery and collection fiber optics at fixed distances of separation between them, (source-collection distance, scd) of 10, 15, 20, 25 and 30 mm.
3. Imaging Spectrograph Component The dispersion/filtering stage consists of an f/1.8 holographic imaging spectrograph with a kinematically exchangeable volume-phase holographic transmission grating providing a 400 nm range centered at 850 nm (Kaiser Optical Systems, Inc., Ann Arbor Mich.).
4. Detector The detector is a computer controlled, thermo-electrically cooled, open-electrode CCD (charge coupled device)[again define this above when term is first used] with 256×1024 pixels, each 25×25 µm in area (Andor Technology, LLC, Belfast, Northern Ireland).
Data Acquisition Routine to Maximize the Signal to Noise Ratio (S/N) within CCD Dynamic Range The first step in the data acquisition sequence, which is controlled by the data acquisition program of the current invention, is a preliminary acquisition made to estimate the single-exposure time (exp) required to maximize the signal-to-noise ratio (S/N) within the linear dynamic range of the detector (about 50000 counts for the CCD of the current invention operated at a gain corresponding to the read-rate of 16 microseconds):

The parameter denoting the preliminary acquisition time is "acq" (0.021 seconds, the minimum achievable at the CCD operating conditions described). The maximum value (counts) of the preliminary spectrum is determined and stored in the variable "max." At the wavelength of max:

$$\max = (I\text{sig} \times \text{acq}) + (I\text{bkg} \times \text{acq})$$

where Isig=the signal intensity, in counts/second
Ibkg=the background intensity, in counts/second
Ibkg is not expected to change from one scd to another or from time to time during a single measurement sequence. An examination of the data shows that this is the case. To avoid making background measurements with each preliminary acquisition, Ibkg is initially taken as 400 (typical for the measurement conditions at the minimum achievable exposure time for the CCD operating conditions, described above). Hence, $$\max = I\text{sig} * \text{acq} + 400 * \text{acq}$$

or $$\max/\text{acq} - 400 = I\text{sig}$$

Exposure time for the first actual data acquisition, at 10 mm scd, is set at exp=50000/Isig, yielding a peak signal intensity of ~50000 counts.

After the 10 mm spectrum is acquired, acq is reset to the exposure time of the 10 mm spectrum, $\text{acq}_{(10\ mm)}$ and Ibkg=400 is replaced by the actual background data acquired for the 10 mm measurement, $\text{Ibkg}_{(10\ mm)}$. Using these values, exp is recalculated as above from a preliminary acquisition for each subsequent measurement yielding actual data acquisition For each measurement, the program executes the following sequence:
1. Execute a preliminary acquisition with integration time=acq and estimate exp as above.
2. Record the CCD operating conditions in log file.
3. Acquire a spectrum with the estimated exposure time (raw).
4. Acquire a background spectrum with same exposure time (bkg).
5. Calculate and store diff spectrum: raw-bkg.
6. Calculate and store cor spectrum: diff/ref.
7. Calculate and store tcor spectrum: cor/exp.

The data acquisition routine described in this example is an improvement over the trial and error method used in Example 2 to maximize S/N in the measurements. This improvement allows shortened total examination time per patient.

Using the device and parameters described in this example, two types of data were acquired: reference data and patient data.

Reference Data

For each source separately, the delivery and collection fiber optics were targeted to a Spectralon® diffuse reflectance standard (Labsphere, Inc., North Sutton, N.H.) in a manner to minimize specular reflectance entering the collection fiber optic to obtain a diffuse reflectance spectrum. The source shutter was opened and data acquisition was initiated for a period of time (exposure time) by entering a computer command. The source shutter was then closed and data acquisition was initiated for an equal exposure time by entering a computer command. Subsequently, the delivery and collection fiber optics were targeted normal to a BaSO$_4$ (barium sulfage) powder sample in a manner to obtain a transmission spectrum similarly (i.e., shutter open data acquisition for transmission exposure time, shutter closed data acquisition for an equal exposure time). The exposure times for the reference spectra data was chosen to maximize the signal to noise ratio (S/N) while maintaining the detected signal level within the linear operating range of the detector, as described in Example 2.

Patient Data

For each source separately, data are acquired at each scd. The elasticized headband was applied to the patient's head so that the template is positioned at the temple, approximately over the pole of the temporal lobe of the brain. The distal end of the delivery fiber optic was inserted into the first template penetration anterior and the distal end of the collection fiber optic was inserted into the second template penetration anterior. The source shutter was opened and data acquisition was initiated for a period of time (exposure time) by entering a computer command. The source shutter was closed and data acquisition was initiated for an equal exposure time by entering a computer command. As for the reference data, the exposure time target was that which maximized S/N while maintaining a linear signal as described in Example 2. Since there was inter-patient variability in the level of the detected signal at each scd, and since there was variability in the level of the detected signal at each scd for each patient, the exposure time was calculated and controlled by software developed for this purpose. The collection fiber optic was removed then inserted into the third template penetration anterior. The source shutter was opened, etc.; this was repeated for each scd, first on one temple then the other, for each patient.

Data Analysis

The reference and patient data acquired by the device in this example were analyzed as follows.

The "shutter closed" data ($S_A$) were subtracted from the corresponding "shutter opened" data ($S_L$) for each acquisition of each type of data (reference and patient), $$S_A = A(\lambda) r(\lambda) D(\lambda) t$$

$$S_L = [I_0(\lambda) + A(\lambda)] r(\lambda) D(\lambda) t,$$

where $I_0(\lambda)$ is the source light intensity incident on the target, $A(\lambda)$ is the ambient light intensity incident on the target, $r(\lambda)$ is the reflectance of the target, $D(\lambda)$ is the detector response function and t is the total exposure time. In this example, the background corrected (c) transmission/reflectance reference (TR) spectrum for each source (s) is calculated as follows:

$$_s^{Nc}S_{TR}(\lambda) = {}_s^c S_{TR}(\lambda) / \int_s^c S_{TR}(\lambda) d\lambda,$$

where $$_s^c S_{TR}(\lambda) = ({}_s^c c_{TR}(\lambda) / \int_s^c c_{TR}(\lambda) d\lambda)^c S_R(\lambda) \text{ and}$$

$$_s^c c_{TR}(\lambda) = [{}^s I_0'(\lambda) T_{BaSO_4}(\lambda) t_T t_T^{-1} / {}^s I_0'(\lambda) r_R(\lambda) D(\lambda) t_R t_R^{-1}],$$

where $T_{BaSO4}$ is the transmission spectrum of barium sulfate measured with the device and $r_R$ is the reflectance spectrum of the reflectance standard measured with the device. Again, the background corrected patient spectra are rectified for exposure time, as above $$_s^{l,d,t}S_P^i = {}_s^{l,d,c}S_P^i / {}_s^{l,d} t_P^i$$

Here, the transmission/reflectance corrected diagnostic patient spectrum $^{TR}S_P$, is $$^{TR}S_P = ({}^t S_P)({}^N S_{TR}),$$

where other indices have been dropped to simplify notation.

Figure 7:
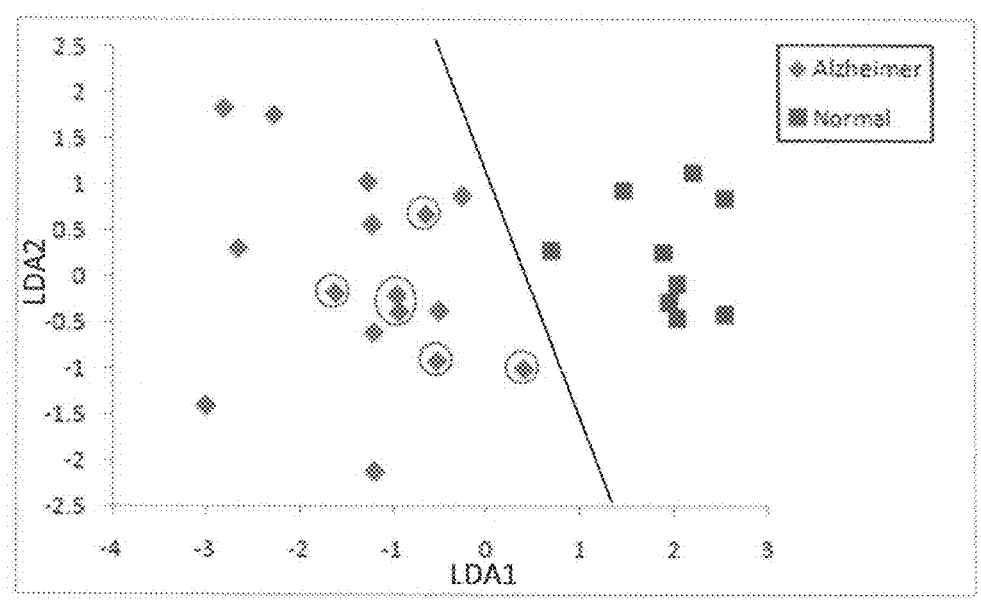
FIG. 7. Plot of intensity at intensity at 800 nm. If a subject's numerical measure i.e., the point (LDA1, LDA2), fell below the plotted line, the patient was spectroscopically diagnosed as having AD. If a subject's numerical measure was above the plotted line, the patient was spectroscopically diagnosed as normal. Subjects clinically diagnosed as normal are indicated by square (blue) and subjects clinically diagnosed as having AD are indicated by diamond (red).

Linear discriminant analysis (LDA) of patient data was performed using two spectroscopic discriminants calculated from each patients spectrum, which was the average of the left and right temple spectra acquired with each source: the intensity at 800 nm of $'S_P^{i}/'S_P^{i'}$ and the slope of $^{TR}S_P$ at 800 nm, calculated from the least squares fit over a range of 10λ. The values of LDA1 and LDA2 calculated from these discriminants using the software environment R for statistical computing (www.r-project.org/) are plotted in FIG. 7 and represent individual subjects. If a subject's numerical measure i.e., the point (LDA1, LDA2), fell below the plotted line, the patient was spectroscopically diagnosed as having AD. If a subject's numerical measure was above the plotted line, the patient was spectroscopically diagnosed as normal. Subjects clinically diagnosed as normal are indicated by square (blue) and subjects clinically diagnosed as having AD are indicated by diamond (red). As shown in the plot, spectroscopic diagnosis correlated with clinical diagnosis of normal or AD with 100% accuracy. Of the 16 clinically diagnosed AD subjects represented, six subsequently came to autopsy. Each of the six (100%) received a neuropathologically confirmed diagnosis of AD (circled diamonds in FIG. 7).

Example 5

This example contemplates using yet another four component device, similar to the devices described in Examples 2 or 3, to demonstrate using near-infrared spectroscopy to detect brain disease in vivo.

The device comprising four components, described in detail below, will be used to acquire spectra data on the subjects with and without probable AD. Spectra from a range of about 486-1037 nm will be acquired with a NIR spectrometer.

Methods

Spectra data will be acquired on patients presenting with concerns about memory or cognitive issues, as part of their routine clinical assessment. Informed consent will be obtained as approved by the Bedford VA Medical Center IRB or other appropriate institutions IRB 1. Light Source and Dispersion Component The light source will be a 50 W, stabilized, tungsten halogen lamp (e.g., from Newport Corp., Irvine, Calif.). A diode laser will be included providing narrowband output centered at 650±0.2 nm with a linewidth of approximately 0.05 nm. (This laser will be developed and manufactured according to our requirements and specifications e.g., by Process Instruments, Inc.).

2. Light Delivery and Collection Optics Component

The delivery fiber optic will be 1 to 3, 3 m, acrylate jacketed, flex-cabled, 200 to 600 µm core, low —OH, silica fibers in a close packed arrangement and standard SMA or other appropriate connector at the distal end and bifurcated or trifurcated proximally as necessary, to accommodate coupling optics from up to three different sources simultaneously and with high-power SMA or other appropriate connectors at the proximal end.

The distal ends of the delivery and collection fiber optics will be integrated into a headpiece that will be positioned on the patient's head and will fix the positions of the delivery and collection fiber optics with respect to the patient's head and will maintain a constant and reproducible contact pressure and angle of the delivery and collection fiber optics with respect to the patient's head.

The distal end of the collection fiber optic will be branched as necessary to provide from 1 to five or more branches, each of which will consist of 1 or more polyimide or acrylate or other appropriate material jacketed, 100 to 200 µm core, low —OH, silica fibers in close packed arrangements and with standard SMA or other appropriate connectors at the distal ends of each branch. The distal ends will be fixed in a linear array, positioned 1-30 mm center to center, in a template that will fix the position of the collection fibers relative to the patient's head for the duration of data acquisition.

3. Imaging Spectrograph Component

The dispersion/filtering component will be a f/1.8 holographic imaging spectrograph with a kinematically exchangeable volume-phase holographic transmission grating providing a 400 nm range centered at 850 nm coupled with a holographic notch pre-filtering stage centered at 647 nm (e.g., from Kaiser Optical Systems, Inc., Ann Arbor Mich.).

Alternatively, the dispersion/filtering will have a solid state on-chip grating.

4. Detector

The detector will be individual detectors comprising a computer controlled, thermo-electrically cooled, back illuminated, deep depletion CCD (charge coupled device) with 256×1024 pixels, each 25×25 µm in area (e.g., from Andor Technology, LLC, Belfast, Northern Ireland).

Using the device described in this example, reference data and patient data will be acquired as described in Example 2, above, except that for each source, data for all scd on each temple will be acquired simultaneously.

Data Analysis

The reference and patient data acquired by the device in this example will be analyzed as described in Example 3 or Example 4, above, with the following changes.

A physical chemical model of the patient spectrum in vivo will be developed, which will enable the quantitative or semi-quantitative extraction of information about the microscopic structure and biochemical composition of the brain, which will be used to enable a neuropathological assessment to arrive at definitive diagnosis with regard to detection and identification of disease or injury and progression/regression of disease or injury over time or in response to experimental therapeutics.

For example, we are developing a data analysis method, which combines the diffusion approximation (DA) [Ishimaru A, 1978; Farrell et al., 1992] with the small angle diffusion approximation (SADA) [Rossi and Greisen, 1941], that can disentangle the brain tissue spectrum from overlying tissue effects. The application of DA alone for this purpose is inappropriate because CSF is not optically diffuse and therefore can not be described accurately by the diffusion approximation. We are developing a mathematical model of light transport in the human head that goes beyond the diffusion approximation.

Here, we summarize the key features. We consider a three-layer system. The first layer (scalp/skull, since we do not know precisely optical properties of skin and skull separately) has thickness $l_1$ and is turbid, the second layer has thickness $l_2$ and is essentially transparent (CSF) and the third layer (cortex) is turbid once again and is semi-infinite. We assume that an infinitely thin beam is incident perpendicularly onto the three-layer medium and that the beam is scattered isotropically at a depth of $z=z_0=1/(\mu_{si}'+\mu_{ai})$, where $\mu_{si}'$ and $\mu_{ai}$ are the reduced scattering and absorption coefficients of layer i, respectively. The origin of the coordinate system is the point where the beam enters the turbid medium and the z coordinate has the same direction as the incident beam. The x and y coordinates lie on the surface of the turbid sample and $\rho=(x^2+y^2)^{1/2}$.

The description of light transport in both turbid layers is relatively straightforward and can be done using the diffusion approximation with appropriate boundary conditions. Light propagation in the less turbid layer (CSF) is more complex. The scattering length in CSF is on the order of 1 cm. Since the CSF layer is only several mm thick, the diffusion approximation is inapplicable. A better choice is the small angle diffusion approximation (SADA) [Rossi and Greisen, 1941]. We combined SADA with the diffusion approximation in the two turbid layers. After introducing the boundary conditions on the outer surface of the scalp and in the infinity, and introducing the appropriate boundary conditions on the two surfaces of the CSF layer, we find a system of three equations that can be solved numerically. Here, we provide an approximate solution in which the middle layer is taken to be transparent. This solution relates the optical spectrum measured on the surface of the head to the optical properties of the gray matter layer. We contemplate employing this solution by designing a numerical algorithm for extracting brain optical properties from the signal measured non-invasively at the surface of the scalp. The parameter that describes the optical properties of the gray matter layer is the diffusion coefficient $D_i$, related to absorption and scattering in the following way, $D_i=\frac{1}{3}(\mu_{ai}+\mu_{si}')$.

Thus our goal will be to calculate $D_3$ from the signal measured on the surface, which is $$R_1 = -\frac{\partial \Phi_1(z=0)}{\partial z}. \tag{1}$$

Using the diffusion approximation with appropriate boundary conditions we can describe light transport in both turbid layers. In this case the variable we will use is fluence rate Φ r (measured by watts per square centimeter), which is related to the specific intensity of light I(r,s) in the following way:

$$\Phi(r) = \int_{4\pi} I(r,s) d\Omega \tag{2}$$

To describe scattering in the non-turbid CSF, we combine SADA with diffusion in the two adjacent layers:

$$D_1 \Delta \Phi_1(r) - \mu_{a1} \Phi_1(r) = -\delta(x, y, z - z_0), \quad 0 \leq z < l_1 \tag{3}$$

$$\left[\left(1 - \frac{s_\perp^2}{2}\right)\frac{\partial}{\partial z} + s_\perp \nabla_r + \mu_{a2}\right] I_2(r, s_\perp) = \frac{\sigma \beta_2}{4} \Delta_{s_\perp} I(r, s_\perp) \quad l_1 \leq z < l_2$$

$$D_3 \Delta \Phi_3(r) - \mu_{a3} \Phi_3(r) = 0, \quad l_2 \leq z$$

This set of equations should be supplemented by the boundary conditions.

$$\Phi_1(x, y, -z_b) = 0 \tag{4}$$

$$I_1(x, y, l_1, s) =$$

$$\left(1 - R_{12}\left(\frac{n_1}{n_2}\right)\right) I_2(x, y, l_1, s') + R_{12}\left(\frac{n_1}{n_2}\right) I_1(x, y, l_1, s'')$$

$$I_2(x, y, l_2, s) = \left(1 - R_{23}\left(\frac{n_2}{n_3}\right)\right) I_3(x, y, l_3, s') + R_{23}\left(\frac{n_2}{n_3}\right) I_{12}(x, y, l_2, s'')$$

$$\Phi_3(x, y, \infty) = 0$$

Here $R_{12}$ and $R_{23}$ are reflection coefficients, which depend on refractive indexes of adjacent layers $n_i$. System (3) with boundary conditions (4) can be solved numerically. The algorithm relates optical properties of each layer to the experimentally measured spectrum. By fitting this model to experimental data, we will be able to extract morphological and biochemical characteristics of the cortex which indicate the presence or absence of disease processes or brain damage. Here we consider an approximate solution in which the middle layer is assumed to be transparent. In this case, intensities in the first and third layers for non-reflected light can be related in the following way:

$$I_3(x, y, s_x, s_y) = I_1(x', y', s_x, s_y) \tag{5}$$

where $$x' = x - \frac{s_x l_2}{\sqrt{1 - s_x^2 - s_y^2}}, \text{ and } y' = y - \frac{s_y l_2}{\sqrt{1 - s_x^2 - s_y^2}}.$$

It appears that the CSF layer may behave as a waveguide, since light can be reflected from its boundaries multiple times.

Here we will limit ourselves to first order effects. Since diffusion equations for the first and third layers are formulated in terms of fluence rates, not intensities, we formulate (5) in terms of fluence rates. Since fluence rates are integral quantities of intensity in the diffuse layers over all possible angles and light distribution in the diffusion approximation is isotropic, we can simply integrate Eq. (5) over all angles:

$$\Phi_3(x, y) = \frac{1}{4\pi} \int_S \frac{dx' dy'}{\sqrt{(x - x')^2 + l_2^2} + \sqrt{(y - y')^2 + l_2^2}} \Phi_1(x - x', y - y') \tag{6}$$

Thus we end up with the following set of equations:

$$D_1 \Delta \Phi_1(r) - \mu_{a1} \Phi_1(r) = -\delta(x, y, z - z_0) \quad 0 \leq z < l_1 \tag{7}$$

$$D_3 \Delta \Phi_3(r) - \mu_{a3} \Phi_3(r) = 0 \quad l_2 \leq z$$

and boundary conditions:

$$\Phi_1(x, y, -z_b) = 0 \tag{8}$$

$$\Phi_3(x, y, l_2) =$$

$$\frac{1}{4\pi} \int_S \frac{dx' dy'}{\sqrt{(x - x')^2 + l_2^2} + \sqrt{(y - y')^2 + l_2^2}} \Phi_1(x - x', y - y', l_1)$$

$$\Phi_3(x, y, \infty) = 0$$

After applying two-dimensional Fourier transform $$\phi_i(z, \xi, \zeta) = F\langle \Phi_i(z, x, y) \rangle \tag{9}$$

$$= \int_{-\infty}^{+\infty} \int_{-\infty}^{+\infty} \Phi_i(z, x, y) \exp[i(x\xi + y\zeta)] dx dy$$

system (7) with boundary conditions (8) has an approximate analytical solution $$\phi_1(z, \tau) = \frac{\sinh[\alpha_1(z_b + z_0)]}{D_1 \alpha_1} \frac{D_1 \alpha_1 \cosh[\alpha_1(l_2 - z)] + D_3 \alpha_3 \cosh[\alpha_1(l_2 - z)]}{D_1 \alpha_1 \cosh[\alpha_1(l_2 - z_b)] + D_3 \alpha_3 \cosh[\alpha_1(l_2 - z_b)]} - \frac{\sinh[\alpha_1(z_0 - z)]}{D_1 \alpha_1} \quad 0 \leq z < z_0 \tag{10}$$

$$\phi_2(z, \tau) = \frac{\sinh[\alpha_1(z_b + z_0)]}{D_1 \alpha_1} \frac{D_1 \alpha_1 \cosh[\alpha_1(l_2 - z)] + D_3 \alpha_3 \cosh[\alpha_1(l_2 - z)]}{D_1 \alpha_1 \cosh[\alpha_1(l_2 - z_b)] + D_3 \alpha_3 \cosh[\alpha_1(l_2 - z_b)]} \quad 0 \leq z < l_1$$

$$\phi_3(z, \tau) = \frac{1}{S} \frac{\sinh[\alpha_1(z_b + z_0)] \exp[\alpha_3(l_2 - z)]}{D_1 \alpha_1 \cosh[\alpha_1(l_2 + z_b)] + D_3 \alpha_3 \cosh[\alpha_1(l_2 + z_b)]}$$

where $\alpha_i^2 = (D_i \tau^2 + \mu_{ai})/D_i$ and $\tau^2 = \xi^2 + \zeta^2$.

By calculating the diffusion coefficient of the cortex layer $D_3$ from system (10) we can find concentrations, average sizes, etc., of neuropathological features in the cortex layer. We contemplate improving this model by increasing the number of overlying layers, including subcortex and adjusting approximations used in deriving Eq. (10).

Alternatively, the method described in Example 2 will use the values of $I_{\lambda(max)}$ and $I_{\lambda(max)}/I_{\lambda(min)}$ to compute Fisher's discriminants and apply Bayesian prior probabilities to create a training set for linear discriminant analysis of $S_P$ and to establish the cut-off for values of the discriminant functions which classify a newly measured $S_P$, thereby predicting whether that patient has or doesn't have AD (or other neurodegenerative disorder, mild traumatic brain injury).

Alternatively, the method described in Example 3 will be used to calculate $S_P'=dS_P(\lambda)/d\lambda$ and compute Student's t-value for $S_P'$ at each wavelength over the range of $S_P$ for control and AD patients and establish a correlation between $S_P'$ and diagnosis.

Example 6

This example shows data demonstrating the use of near-infrared spectroscopy to detect precursive brain disease in vivo and to detect and differentiate two different brain diseases in vivo
Detection of Mild Cognitive Impairment (MCI)

The data in this example shows the detection of MCI in patients. This is important since in many instances, MCI cases progress to AD over time and current consensus suggests clinical MCI, particularly amnestic-MCI, may constitute an early stage of AD. Therefore, the ability to characterize MCI subjects spectroscopically represents the potential for early NIR optical spectroscopic detection of AD.

Figure 8:
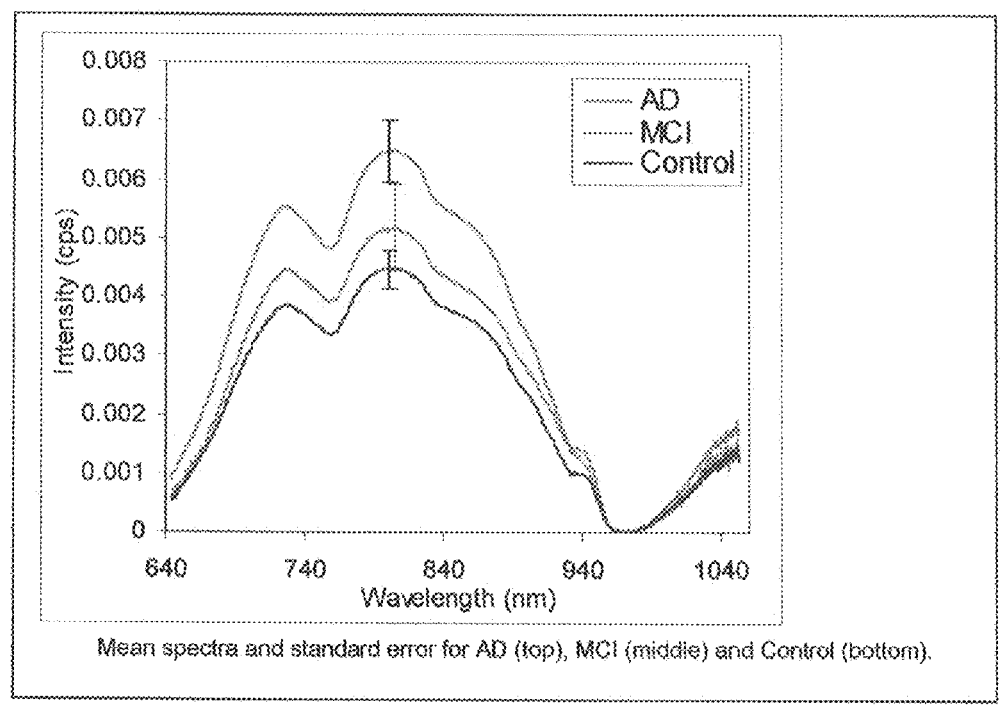
FIG. 8 is a line graph and shows the mean of spectra acquired at sdc=20 mm for AD, MCI and control (normal) subjects. The intensity differences apparent in FIG. 8 are conserved for the total integrated intensities and significantly differentiate AD from control: p=0.001128 at s-d=20 mm and p=0.001018 at s-d=25 mm. (Error bars=standard error.)

In FIG. 8 we show the mean of spectra acquired at sdc=20 mm for AD, MCI and control (normal) subjects. It is readily apparent that the intensity at about 800 nm differentiates AD from MCI from Control cases significantly. Also, since the intensities at about 970 nm are approximately equal, long wavelength "slope," or relative intensities, also distinguish these three groups. Notably, the intensity and "slope" for the MCI subjects falls between the AD and control groups. The intensity differences apparent in FIG. 8 are conserved for the total integrated intensities and significantly differentiate AD from control: p=0.001128 at s-d=20 mm and p=0.001018 at s-d=25 mm. (Error bars=standard error, all Figs.)

Figure 9A:
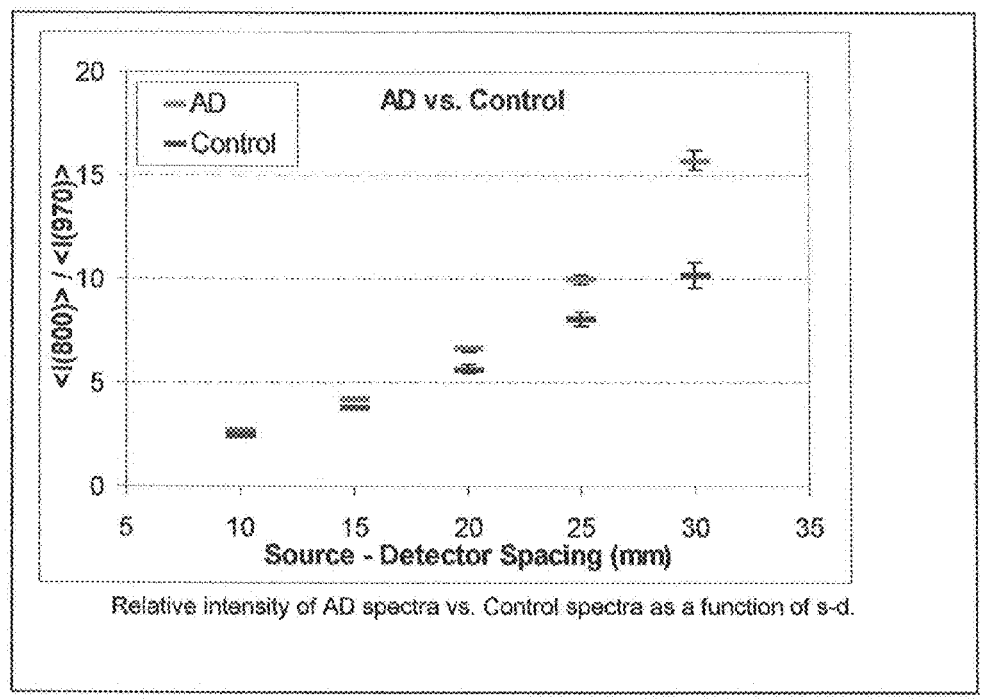
FIG. 9 $a$, $b$, $c$, shows the ratio of the intensity at 800 nm (wavelength of maximum intensity) to the intensity at 972 nm (a minimum) at five scd for AD vs. Control, MCI vs. Control and AD vs. MCI, respectively. The p-value for differentiating MCI from control was p=0.011 at scd=30 mm. (Error bars=standard error, all Figs.)
Figure 9B:
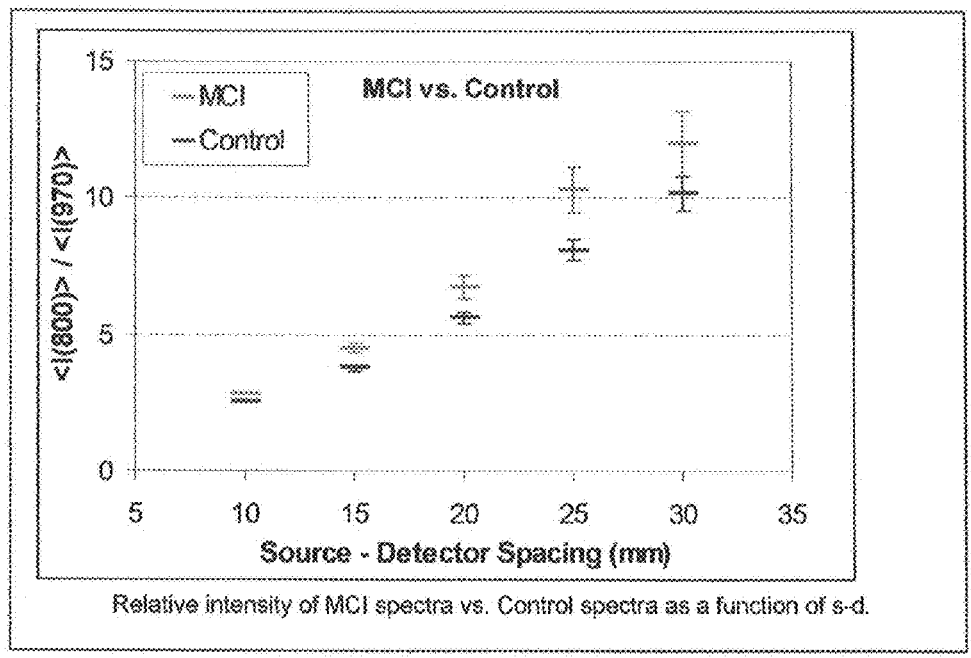
Figure 9C:
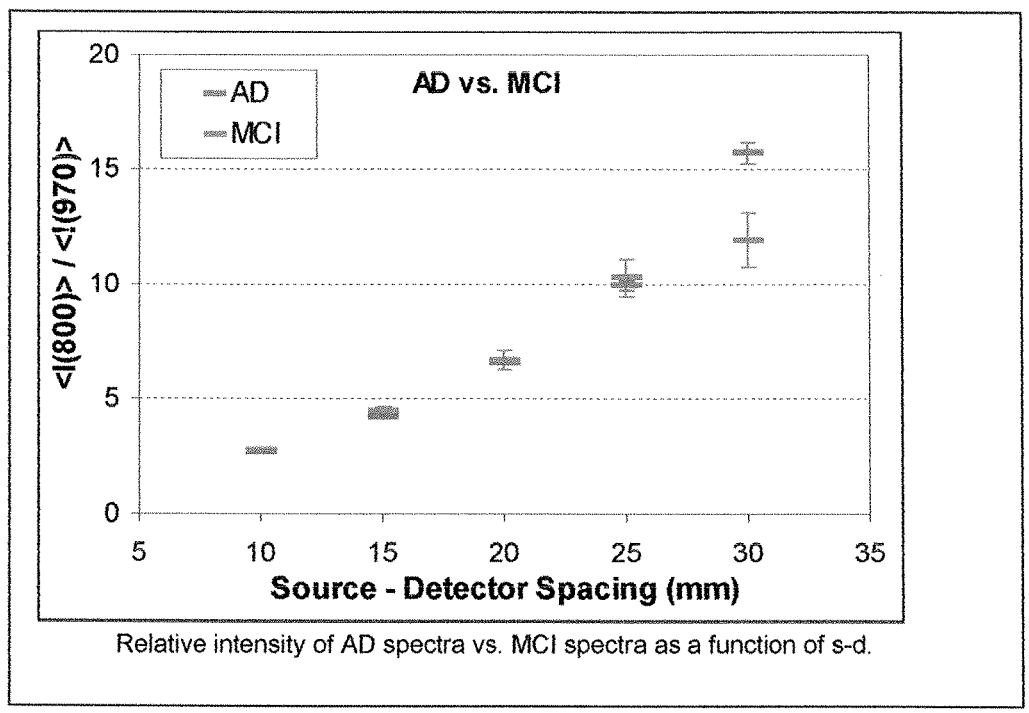

The relative intensity ratio I800/I970 differentiates AD from control and MCI from control. In vitro, neuropathologic features affect the wavelength dependence in a specific and characteristic manner, analogous to small particle (Mie) scattering. In vivo, this is evidenced by the relative intensities within the spectra, in effect, the long wavelength slope. In FIG. 9 a, b, c, we examine the ratio of the intensity at 800 nm (wavelength of maximum intensity) to the intensity at 972 nm (a minimum).

Clearly, the particle scattering contribution to the in vivo spectrum, which we assign to the presence of structures such as plaques, tangles and Lewy bodies, is a powerful discriminant between AD, MCI and control spectra. The statistical significance of the results for AD versus control and MCI versus control are p=0.0186 at scd=25 mm and p=0.011 at scd=30 mm, respectively, and we expect that the p-value for MCI vs. control will improve significantly as the number of MCI subject spectra increases. For completeness, we include the results for MCI vs. AD, though clinically there is less significance or difficulty in distinguishing MCI patients from probable AD patients.

The p-values for differentiating MCI from control improved as more MCI subjects were measured, as we had predicted. Using the same analysis as above (FIG. 9b), the p-value for MCI vs. control improved to p≤0.01.

To obtain the results in Table 2 we performed LDA using the R statistical analysis programming environment, as described in Example 4, specifying AD and control as two groups a priori (in the table, CTL=Control and < >=mean value). Spectra were normalized to unit integrated intensity, similar to Example 3, Data Analysis, thus removing signal intensity as a factor. This is desirable because measurement variability (fiber optic contact and positioning, light-source output, etc.) can confound inter-subject biological variability. Instead, the intra-spectrum wavelength dependent intensity, i.e., the spectroscopic line shape, was analyzed. A linear discriminant function was calculated to maximize separation between AD and control groups. This discriminant function was then used to convert the MCI spectra to scores, an approach which does not presuppose that MCI subjects are a distinct group. Parametric statistical analysis of the scores for the three groups yields the results tabulated in Table 2. As can be seen, MCI subjects are significantly different from AD and control subjects.

TABLE 2

| <AD> | <CTL> - <AD> | std. dev. AD | p (AD v. CTL) |
|---|---|---|---|
| −1.504841 | 3.13509 | 1.106738 | 8.049058e−15 |
| <MCI> | <CTL> - <MCI> | std. dev. MCI | p (MCI v. CTL) |
| 0.153875 | 1.47637 | 0.9324275 | 0.0005707991 |
| <CTL> | <MCI> - <AD> | std. dev. CTL | p (AD v. MCI) |
| 1.630244 | 1.65872 | 0.8692399 | 0.0002195560 |

CTL = control,
AD = Alzheimer disease,
DLB = dementia with Lewy bodies,
LB = Lewy body(ies),
NP = neuritic plaque,
LDA = linear discriminant analysis, and
MCI = mild cognitive impairment.

Differentiation of DLB from AD

Alzheimer's disease is the most common form of neurodegenerative dementia seen in clinical practice and current consensus is that DLB is the second most common AD, DLB, vascular dementias, etc. may have overlapping neuropathologic and clinical aspects with potentially differing therapeutic implications and distinction between them is important because of potentially differing therapeutic implications and prognosis. For example, neuroleptics, frequently used to control symptoms in dementia such as hallucination or severe agitation, may be contraindicated in DLB due to the significantly greater likelihood of severe adverse reaction, including untimely death. Therefore, spectroscopic differentiation of AD and DLB can serve as both a useful and limiting test.

Figure 10:
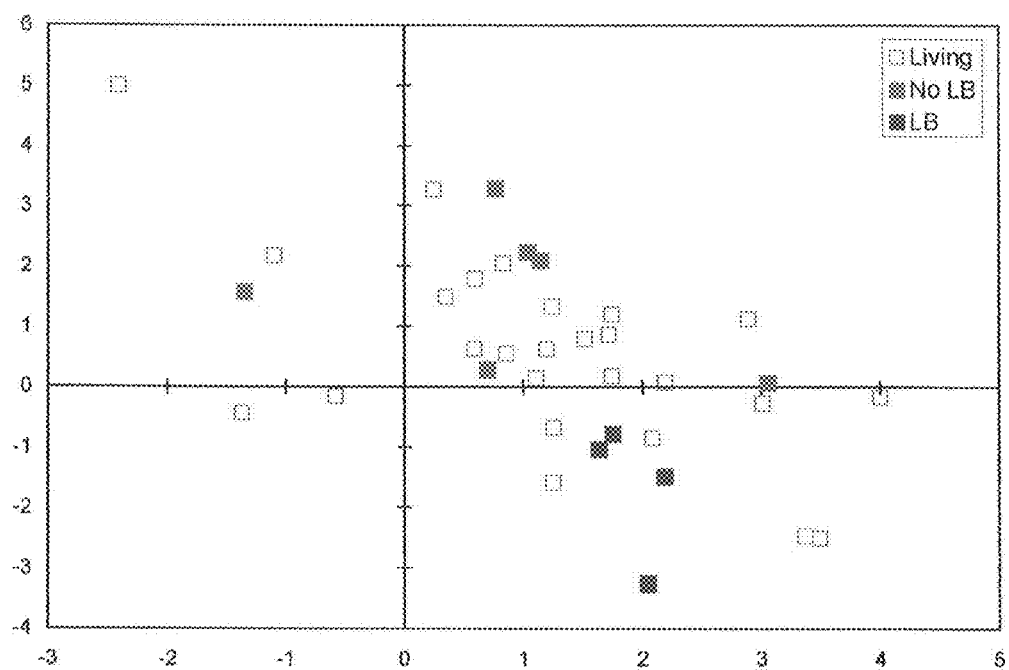
FIG. 10. Spectra acquired in vivo for dementia in patients with cortical Lewy bodies (indicative of DLB) confirmed at autopsy, even with a high degree of overlapping neuritic plaque pathology (indicative of AD), are clearly differentiated from those who showed no LB at autopsy. Red squares, cortical LB confirmed at autopsy; blue squares, no cortical LB found at autopsy; open squares, still living patients.

Table 3, below, presents neuropathology findings in temporal cortex for study subjects who have come to autopsy. The scatter plot in FIG. 10 shows LDA, as described in Example 4, of in vivo spectra from the last data set which contained spectra for all five subjects. Left and right temple spectra in vivo, of each subject whose clinical diagnosis was probable AD, are represented separately. Spectra acquired in vivo for patients with confirmed cortical Lewy bodies (indicative of DLB), even with a high degree of overlapping neuritic plaque pathology (indicative of AD), are clearly differentiated from those who showed no LB at autopsy (FIG. 10).

TABLE 3

|  | AD pathology | Plaque density | Lewy bodies |
|---|---|---|---|
| Pat. #1 | high | frequent | 0 |
| Pat. #2 | high | frequent | 10 |
| Pat. #3 | intermediate | frequent | 16 |
| Pat. #4 | high | frequent | 0 |
| Pat. #5 | high | frequent | 0 |

CTL = control,
AD = Alzheimer disease,
DLB = dementia with Lewy bodies,
LB = Lewy body(ies),
NP = neuritic plaque,
LDA = linear discriminant analysis, and
MCI = mild cognitive impairment.

Example 7

A technique which relates the spectrum of visible and near-infrared light reflected from brain tissue to its basic morphological and biochemical characteristics follows. This technique has three parts: (1) the first part relates basic morphological and biochemical characteristics of tissue to optical absorption and scattering; (2) the second part describes light transport in turbid media and takes into account the light delivery and collection geometry; (3) the third part, which uses parts one and two to model the patient spectrum, $S_P(\lambda)$, fits the model to experimental data to extract tissue characteristics.

In the first part, we assume that scattering of light in brain tissue can be approximated as scattering on spherical centers of various sizes D and refractive indices n. We also assume these scattering centers have a bimodal Gaussian size distribution. (In this example, smaller particles have $D_s$ less than one micron, and bigger particles have $D_b$ more than one micron, in diameter. In this example, the widths of the distributions are fixed at $\Delta \approx 0.1 \cdot D$)) We describe the reduced scattering coefficient of the tissue, $\mu_s'(\lambda)$, in terms of the scattering centers using Mie theory, which provides an exact analytical solution for scattering of a plane wave by a sphere and also provides a first-order description of optical effects in non-spherical particles [Bohren and Huffman, 1983].

$$\mu_s'(\lambda) = N_s \int_V G\left(\frac{D-D_s}{\Delta_s}\right) \mu_{s,Mie}'(D, n_s, \lambda) d^3 D + N_b \int_V G\left(\frac{D-D_s}{\Delta_b}\right) \mu_{s,Mie}'(D, n_b, \lambda) d^3 D \quad (1)$$

We represent the absorption coefficient, a, of the tissue as a linear combination of known absorption coefficients for the main tissue absorbers in this wavelength region, oxyhemoglobin, deoxyhemoglobin, water and lipid, with the concentrations of each absorber, $c_i$, as the expansion coefficients:

$$\mu_a(\lambda) = \sum_{i=1}^{4} c_i \mu_{a,i}(\lambda) \quad (2)$$

In the second part, we use our description of brain tissue optical properties to develop a model for light propagation in brain tissue, which incorporates a solution for the diffusion approximation R. Starting with an expression derived by Farrell, Patterson and Wilson [Farrell et al., 1992], we obtained a simple analytical expression for the diffuse reflectance at distances r from the source (i.e., at different scd):

$$R_d(\lambda, r) = \frac{z_0}{4\pi} \frac{\mu_s'}{\mu_s' + \mu_a}\left[\left(\mu + \frac{1}{r_1}\right)\frac{\exp(-\mu r_1)}{r_1^2} + \left(1 + \frac{4}{3}A\right)\left(\mu + \frac{1}{r_2}\right)\frac{\exp(-\mu r_2)}{r_2^2}\right],$$

where, $$\mu = [3\mu_a(\mu_s' + \mu_a)]^{\frac{1}{2}},$$

$$z_0 = [\mu_s' + \mu_a]^{-1},$$

$$r_1 = (z_0^2 + r^2)^{\frac{1}{2}},$$

$$r_2 = \left(z_0^2\left(1 + \frac{4}{3}A\right)^2 + r^2\right)^{\frac{1}{2}}.$$

The parameter A depends on the relative refractive index n of the medium and in the case of brain tissue in air is approximately A=3.2 [Zonios et al, 1996]. The fiber optic probe of our device is measuring reflectance at several scd, so we use expression (3) to construct a system of equations $$R_m(r_i, \lambda) = R_d(\lambda, r), i = 1, 2, 3 \ldots \quad (4)$$

where $R_m$ is the experimentally measured diffuse reflectance and index i denotes scd.

Thus we have enough equations to extract both $\mu_a(\lambda)$ and $\mu_s'(\lambda)$ of brain tissue. Combining parts one and two, we arrive at our model for the spectrum of light diffusely scattered from brain tissue:

$$S_P(\lambda) = I_0(\lambda) \iint R[\mu_a(\lambda), \mu_s'(\lambda), r_1 - r_2] dr_2 dr_1 \quad (5)$$

where the light delivery and collection geometry are accounted for in the integration over $r_1$ and $r_2$, the delivery and collection spots for one pair of scd [iii].

In the third part, we use least squares minimization to fit the model to experimental data and extract the following tissue characteristics: average sizes, refractive indexes, and number densities of two types of scattering centers, concentration of oxyhemoglobin and concentration of lipids. We also apply these physical constrains: absorber concentrations and the sizes and number densities of scattering centers can not be negative; the total volume of the scattering centers can not be greater than the total tissue volume; refractive indices, n, of the scattering centers must be in the range 1.35<n<1.5.

From fitting the model to experimental data, we obtain absorber concentrations for $HbO_2$, lipids and water, and the number densities, sizes and refractive indices of two major light scatterers in brain tissue. As an example, results derived from model fits to the spectra of brain tissue specimens, with confirmed neuropathological diagnosis and ApoE genotype, are compiled in Table 4. (Water concentration, found to be ~80% for all specimens, is not tabulated.)

TABLE 4

Physical chemical properties of absorbers and scatterers in brain tissue determined using the device and the method of analysis described in this section. R is radius and n is relative refractive index for the two size distributions of scatterer centers. The table also shows the ApoE status of each case for which data was available.

| Brain # | Diagnosis | n | R (μm) | Concentration | n | R (μm) | Concentration | HbO$_2$ (%) | Lipids | ApoE Status |
|---|---|---|---|---|---|---|---|---|---|---|
| 11 | Control | 1.07 | 0.301 | 1.96E+08 | 1.1 | 1.033 | 0.00E+00 | 9.21 | 0.35468 | |
| 12 | Control | 1.06 | 0.326 | 2.76E+08 | 1.1 | 4.968 | 0.00E+00 | 2.98 | 0.33826 | 3/4 |
| 13 | Control | 1.07 | 1.315 | 5.12E+06 | 1.11 | 3.88 | 2.97E−11 | 2.51 | 0 | |
| 14 | Control | 1.05 | 1.5 | 1.55E+07 | 1.12 | 6.05 | 0.00E+00 | 1.42 | 0 | 3/3 |
| 10 | Lewy Body | 1.07 | 1.5 | 3.08E+06 | 1.12 | 3.42 | 4.34E−11 | 3.1 | 0.33169 | 3/3 |
| 6 | Lewy Body | 1.05 | 0.683 | 1.78E+07 | 1.1 | 8.367 | 5.14E+03 | 5.2 | 1.3399 | 4/4 |
| 5 | Lewy Body | 1.04 | 0.536 | 6.20E+07 | 1.11 | 7.495 | 1.05E+04 | 4.29 | 1.37274 | 3/4 |
| 3 | Lewy Body | 1.06 | 1.126 | 1.38E+07 | 1.11 | 4.605 | 0.00E+00 | 1.81 | 0 | |
| 9 | Lewy Body | 1.04 | 0.349 | 1.51E+08 | 1.11 | 5.494 | 2.15E+04 | 7.57 | 2.32184 | |
| 4 | Alzheimer's | 1.07 | 0.32 | 1.65E+08 | 1.11 | 3.908 | 0.00E+00 | 4.31 | 0 | 2/4 |
| 7 | Alzheimer's | 1.05 | 0.329 | 3.08E+08 | 1.11 | 6.016 | 1.91E+04 | 6.5 | 0 | |
| 8 | Alzheimer's | 1.05 | 0.842 | 9.70E+06 | 1.1 | 7.532 | 7.53E+03 | 4.03 | 2.72578 | |
| 1 | Alzheimer's | 1.05 | 0.363 | 7.62E+07 | 1.1 | 7.27 | 9.50E+03 | 4.71 | 0.33826 | 3/4 |
| 2 | Alzheimer's | 1.06 | 1.5 | 1.87E+06 | 1.1 | 7.625 | 8.77E+03 | 3.47 | 4.63054 | |

These results demonstrate the potential of the invention to obtain quantitative information about the neuropathological features of brain tissue. For all specimens, the dominant scattering centers are small particles (~0.5 μm) of relative refractive index ~1.06. All specimens have high concentrations of such centers. This result is consistent with mitochondrial scattering [Perelman and Backman, 2002], and cortical neurons are among the highest in mitochondrial density in the human body. The other scattering center extracted from the spectra in this example of the invention is a large particle of diameter ~11 μm and refractive index ~1.11. The relative concentration of such particles is zero in the control specimens, $10^3$ in DLB specimens and $10^5$ in AD specimens. The large scatterer particle size agrees with stereological analysis, the major component of plaque size distribution determined by Hyman [Hyman et al., 1995] and the relative refractive index expected for a densely packed protein aggregate [Perelman and Backman, 2002]. The invention detected plaques in neuropathologically confirmed AD cases (7, 8, 1 and 2) and no plaques in control cases (11, 12, 13 and 14). One AD case (4), which showed "intense gliosis, there are few senile plaques suggesting there has been resorption of plaques," (from the autopsy report) and two DLB cases (3 and 10) nominally yielded 0.5 plaques mm$^{-2}$ pathologically and no plaques spectroscopically (large scatterer Concentration=0.0, 0.0 and 4.34×10$^{-11}$, respectively). There is also good agreement between plaques sizes determined by spectroscopy and by histopathology. We conclude that at its present stage, the invention can capture light scattering signatures from senile plaques in brain tissue and can differentiate their concentrations in AD v. DLB brain. DLB is also differentiated from AD and control by the small scatterer. The median small scatterer diameter for DLB tissue is twice that of AD and control tissue, probably indicating the contribution of Lewy bodies to the scattering signature, though we have not yet confirmed this pathologically. The methods herein may enable finer resolution of scattering features to improve scattering center size and number density determinations, to include scattering center shape as another means of differentiating dementias and to identifying other pathological variables such as neuronal density. With coupling to the light transport model described Example 5 the methods herein may contribute to a method for extracting quantitative information about brain tissue neuropathology enabling quantitative diagnosis and monitoring of neurodegenerative diseases in vivo.

REFERENCES

Irizarry M C, Hyman B T, "Alzheimer Disease Therapeutics," *J Neuropath Exp Neurol*, 60, 923-8 (2001).

Coimbra A, Williams D S, Hostetler E D, "The role of MRI and PET/SPECT in Alzheimer's disease," *Curr Top Med Chem*, 6, 629-47 (2006).

Machulda M M, Ward H A, Borowski B, Gunter J L, Cha R H, O'Brien P C, Petersen R C, Boeve B F, Knopman D, Tang-Wai D F, Ivnik R J, Smith G E, Tangalos E G, Jack C R J, "Comparison of memory fMRI response among normal, MCI, and Alzheimer's patients," *Neurology*, 61, 500-6 (2003).

Jack C R J, Shiung M M, Weigand S D, O'Brien P C, Gunter J L, Boeve B F, Knopman D S, Smith G E, Ivnik R J, Tangalos E G, Petersen R C, "Brain atrophy rates predict subsequent clinical conversion in normal elderly and amnestic MCI," *Neurology*, 65, 27-31(2005).

Mathis C A, Wang Y, Klunk W E, "Imaging beta-amyloid plaques and neurofibrillary tangles in the aging human brain," *Curr Pharm Des*, 10, 1469-92 (2004).

Hock C, Villringer K, Muller-Spahn F, Wenzel R, Heekeren H, Schuh-Hofer S, Hofmann M, Minoshima S, Schwaiger M, Dirnagl U, Villringer A, "Decrease in parietal cerebral hemoglobin oxygenation during performance of a verbal fluency task in patients with Alzheimer's disease monitored by means of near-infrared spectroscopy (NIRS)—correlation with simultaneous rCBF-PET measurements," *Brain Res*, 755, 293-303 (1997).

Strangman G, Culver J P, Thompson J H, Boas D A, "A quantitative comparison of simultaneous BOLD fMRI and NIRS recordings during functional brain activation," *Neuroimage*, 17, 719-31 (2002).

Hintersteiner M, Enz A, Frey P, Jaton A, Kinzy W, Kneuer R, Neumann U, Rudin M, Staufenbiel M, Stoeckli M, Wiederhold K, Gremlich H, "In vivo detection of amyloid-beta deposits by near-infrared imaging using an oxazine-derivative probe," *Nat Biotechnol*, 23, 577-83 (2005).

Skoch J, Dunn A, Hyman B T, Bacskai B J, "Development of an optical approach for noninvasive imaging of Alzheimer's disease pathology," *J Biomed Opt*, 10: 11007.

Braak H, Braak E (1991) "Neuropathological staging of Alzheimer-related changes," *Acta Neuropathol (Berl),* 82(4), 239-59 (2005).

Zede E P, Ivanov A P, Katsev I L Image Transfer Through a Scattering Medium, Springer-Verlag Berlin Heidelberg 1991

Van der Zee P, Essenpreis M, Delpy D T, "Optical properties of brain tissue," in *Photon Migration in Random Media and Tissues,* Alfano R R, Chance B, eds, *Proc SPIE* 1888, 454-465 (1993).

Cheong W F, Prahl S A, Welch A J, "A review of the optical properties of biological tissues," *IEEE J Quantum Electron.* 26, 2166-2185 (1990).

Perelman L T, Backman V, Wallace M, et al., "Observation of Periodic Fine Structure in Reflectance from Biological Tissue: A New Technique for Measuring Nuclear Size Distribution," *Phy. Rev Lett,* 80, 627-630 (1998).

Hanlon E B, Itzkan I, Dasari R R, Feld M S, Ferrante R J, McKee A C, Lathi D, Kowall N W, "Near infrared fluorescence spectroscopy detects Alzheimer's disease in vitro" *Photochem Photobio,* 70, 236-242 (1999). Jobsis-vander Vliet, F F.

Jobsis-vander Vliet, F F. Discovery of the near-infrared window into the body and the early development of near-infrared spectroscopy J Biomed Optics 1999; 4: 392-396.

Jobsis F F. Noninvasive near-infrared monitoring of cerebral and myocardial oxygen sufficiency and circulatory parameters. Science 1977; 198:1264-1267.

Love S. Neuropathological investigation of dementia: A guide for neurologists. J Neurol Neurosurg Psychiatry 2005; 76(Suppl V):v8-v14.

Okada E, Firbank M, Schweiger M, Arridge S R, Cope M, Delpy D T. Theoretical and experimental investigation of near-infrared light propagation in a model of the adult head. Applied Optics 1997; 36:21-31

Morris J C and Price A L. Pathologic correlates of nondemented aging, mild cognitive impairment, and early-stage Alzheimer's disease. J Mol Neurosci 2001; 17:101-118.

Hanlon E B, Perelman L T, Vitkin E, Greco F A, McKee A C and Kowall N W. Scattering differentiates Alzheimer Disease in vitro, Optics Letters, 2008, 33(6):624-626.

Hanlon E B, Siwek D F, Mckee A C, Kowall N W, Fang H, Vitkin E I and Perelman L T. Optical Spectroscopy to Diagnose Alzheimer's Disease In Vivo.

Mathis C A, Wang Y, Klunk W E, "Imaging beta-amyloid plaques and neurofibrillary tangles in the aging human brain," *Curr Pharm Des,* 10, 1469-92 (2004).

Brown S D (1995) "Chemical Systems Under Indirect Observation: Latent Properties and Chemometrics," *Applied Spectroscopy,* 49, 14A-31A.

Kleinbaum D G, Kupper L L, Muller K E, eds. (1988) "Logistic Regression," in *Applied Regression Analysis and Other Multivariable Methods,* Belmont, Calif., USA, Duxbury Press, 512-516.

Ishimaru A, *Wave propagation and scattering in random media.* Orlando, Fla.: Academic Press; 1978.

Farrell T J, Patterson M S, and Wilson B C, A diffusion theory model of spatially resolved, steady-state diffuse reflectance for the non-invasive determination of tissue optical properties, *Med. Phys.* 19, 1992, 879-888.

Rossi B, Greisen K (1941) *Rev Mod Phys* 13, 241.

George Zonios, Lev T. Perelman, Vadim Backman, Ramasamy Manoharan, Maryann Fitzmaurice, Jacques Van Dam, and Michael S. Feld "Diffuse Reflectance Spectroscopy of Human Adenomatous Colon Polyps In Vivo" Applied Optics, Vol. 38, Issue 31, pp. 6628-6637]

Fisher, R. (1936). The use of multiple measurements in taxonomic problems. Annals of Eugenics, 7, 179-188.]

P. Fischer, S. Jungwirth, S. Zehetmayer, S. Weissgram, S. Hoenigschnabl, E. Gelpi, W. Krampla and K. H. Tragl. Conversion from subtypes of mild cognitive impairment to Alzheimer dementia. *Neurology* 2007; 68: 288-291

Bohren C F and Huffman D R. (1983) *Absorption and Scattering of Light by Small Particles* New York: John Wiley & Sons.

Zonios G, Cothren R M, Arendt J T, Wu J, Van Dam J, Crawford J M, Manoharan R, Feld M S (1996) "Morphological Model of Human Colon Tissue Fluorescence," *IEEE Trans. Biomed. Eng.,* 43, 113-122.

Perelman L T and Backman V. (2002) "Light Scattering Spectroscopy of Epithelial Tissues: Principles and Applications" in Tuchin V (ed) *Handbook on Optical Biomedical Diagnostics* Chapter XII, Bellingham: SPIE Press Hyman B T, West H L, Rebeck G W, et al. (1995) "Quantitative analysis of senile plaques in Alzheimer disease: observations of log-normal size distribution and molecular epidemiology of differences associated with apolipoprotein E genotype and trisomy 21 (Down syndrome)" *Proc. Natl Acad Sci USA,* 92, 3586-90.

What is claimed is:

1. A non-invasive method of detecting or evaluating brain damage in a living subject wherein the method comprises:
   (a) exposing a part of the subject's head to a light source comprising a range of wavelengths from visible through near-infrared wavelengths, so as to produce multiple spectra measured at various distances from the light source after the light has propagated through the subject's head;
   (b) characterizing each spectrum of the produced multiple spectra by calculating an intensity at each wavelength of the spectrum and a spectroscopic lineshape by calculating relative intensity at each wavelength of the spectrum produced in step (a);
   (c) selecting an intensity and a slope at one or more wavelengths from a plot of the intensity at each wavelength of the spectrum and the spectroscopic lineshape in step (b); and
   (d) assigning a numerical value to the intensity and the slope in step (c), comparing the numerical values obtained from control subjects known not to have brain damage in question to brain damaged subjects, and detecting a statistically significant difference in the numerical values for brain damaged subjects and control subjects, such a difference being indicative of brain damage;
   wherein the brain damage detected is a mild cognitive impairment (MCI), a dementia with Lewy bodies (DLB), Alzheimer's disease, or a mild traumatic brain injury (mTBI), thereby detecting or evaluating brain damage in the living subject.

2. The method of claim 1, wherein the source emitting light in the visible through near-infrared wavelength range is a xenon lamp, a mercury lamp, a tungsten lamp, a laser, or a combination therapy thereof.

3. The method of claim 1 wherein the method further comprises the assessment of cognitive deficits in the subject.

4. The method of claim 1, wherein the brain damage is Alzheimer's disease.

5. The method of claim 1, wherein the brain damage is a diffuse or mild traumatic brain injury.

6. The method of claim 1, wherein the brain damage is associated with an abnormal accumulation or deposits of proteins or other molecules or with diffuse axonal injury that alters the multiple spectra of step (a) passing through affected tissue.

7. The method of claim 6, wherein the abnormal accumulation or the deposits of proteins or other molecules have resulted in the formation of one or more of cortical neuritic plaques, neurofibrillary tangles, Lewy bodies, lipofuscin granules, amyloid derived diffusible ligands, or neuropil threads.

8. The method of claim 1, wherein the subject is a mammal.

9. The method of claim 8, wherein the mammal is a human.

10. The method of claim 1, wherein the method is used to evaluate a stage or a severity of the brain damage.

11. The method of claim 10, wherein repeated applications of the method over time are used to evaluate a course of the test subject brain damage and/or to evaluate a response of the test subject to treatment, and/or to determine future treatment for the test subject.

12. The method of claim 1, wherein the method used to collect the data is non-invasive.

13. The method of claim 1, wherein a fiber optic assembly delivers the light from the light source to the subject's head.

14. The method of claim 1, wherein a fiber optic assembly is used to collect light received from the head.

15. The method of claim 1, wherein the part of the subject's head to which the light source is directed is the subject's temple.

16. The method of claim 1, wherein the visible through near-infrared wavelength range is from 350 to 2250 nm.

17. The method of claim 16 wherein the visible through near-infrared wavelength range is from 610-1030 nm.

18. The method of claim 1, wherein the light source comprises a distal end and a proximal end, and wherein, in step (a), both the distal end of the light source and the proximal end of the light source are affixed to a solid surface with defined source-to-detector distances.

19. The method of claim 18, wherein the source-to-detector distances are 10, 15, 20, 25 and 30 mm or are selected from the group of 10, 15, 20, 25 and 30 mm.

* * * * *